US009278077B2

(12) United States Patent
DeBrouse

(10) Patent No.: US 9,278,077 B2
(45) Date of Patent: Mar. 8, 2016

(54) MICROENCAPSULATED BIOACTIVE AGENTS FOR ORAL DELIVERY AND METHODS OF USE THEREOF

(71) Applicant: Tamarisk Technologies Group, LLC, Moorpark, CA (US)

(72) Inventor: Daniel R. DeBrouse, Las Vegas, NV (US)

(73) Assignee: TAMARISK TECHNOLOGIES GROUP, LLC, Moorpark, CA (US)

( * ) Notice: Subject to any disclaimer, the term of this patent is extended or adjusted under 35 U.S.C. 154(b) by 0 days.

(21) Appl. No.: 14/051,939

(22) Filed: Oct. 11, 2013

(65) Prior Publication Data

US 2014/0037743 A1 Feb. 6, 2014

Related U.S. Application Data

(63) Continuation of application No. 12/718,424, filed on Mar. 5, 2010, now abandoned, which is a continuation-in-part of application No. 11/938,638, filed on Nov. 12, 2007, now abandoned.

(60) Provisional application No. 61/158,231, filed on Mar. 6, 2009.

(51) Int. Cl.

| | |
|---|---|
| ***A61K 31/05*** | (2006.01) |
| ***A61K 9/50*** | (2006.01) |
| ***A61K 47/02*** | (2006.01) |
| ***A61K 47/10*** | (2006.01) |
| ***A61K 47/26*** | (2006.01) |
| ***A61K 47/36*** | (2006.01) |
| ***A61K 47/44*** | (2006.01) |
| ***A61K 31/035*** | (2006.01) |
| ***A61K 31/122*** | (2006.01) |
| ***A61K 31/375*** | (2006.01) |
| ***A61K 31/573*** | (2006.01) |
| ***A61K 35/745*** | (2015.01) |
| ***A61K 35/747*** | (2015.01) |
| ***A61K 38/28*** | (2006.01) |
| ***A61K 45/06*** | (2006.01) |

(52) U.S. Cl.

CPC ............. *A61K 9/5036* (2013.01); *A61K 31/035* (2013.01); *A61K 31/05* (2013.01); *A61K 31/122* (2013.01); *A61K 31/375* (2013.01); *A61K 31/573* (2013.01); *A61K 35/745* (2013.01); *A61K 35/747* (2013.01); *A61K 38/28* (2013.01); *A61K 45/06* (2013.01); *A61K 47/02* (2013.01); *A61K 47/10* (2013.01); *A61K 47/26* (2013.01); *A61K 47/36* (2013.01); *A61K 47/44* (2013.01)

(58) Field of Classification Search

None

See application file for complete search history.

(56) References Cited

U.S. PATENT DOCUMENTS

| | | | | |
|---|---|---|---|---|
| 5,897,876 | A * | 4/1999 | Rudnic et al. | 424/455 |
| 6,365,185 | B1 * | 4/2002 | Ritschel et al. | 424/473 |
| 7,294,334 | B1 * | 11/2007 | Michal | A61K 9/0024 424/93.1 |
| 2007/0281894 | A1 * | 12/2007 | Gant et al. | 514/28 |

FOREIGN PATENT DOCUMENTS

WO WO 2010/102198 * 9/2010 ............. A61F 13/00

OTHER PUBLICATIONS

Han et al., J. Agric. Food Chem., 2008, 56(7), pp. 2528-2535.*

* cited by examiner

*Primary Examiner* — Brian Gulledge
(74) *Attorney, Agent, or Firm* — Hovey Williams LLP

(57) ABSTRACT

The presently claimed and disclosed inventive concept(s) contemplates a novel polymeric oral dosage form (transmucosal delivery vehicle) for delivery of pharmaceutical and nutriceutical bioactive agents to the mucosa and bloodstream of the intestine. The oral dosage form of the presently claimed and disclosed inventive concept(s) comprises a polymeric coating which encapsulates the bioactive agent and inhibits degradation and dissolution of the bioactive agent within the stomach and within the lumen of the intestine until after passing through the mucosal wall of the small and/or large intestine. The enzymatic degradation of the polymeric delivery vehicle containing the bioactive agent is substantially inhibited until after absorption of the polymeric delivery vehicle into blood vessels of the intestinal mucosa. It is a particular object of the presently claimed and disclosed inventive concept(s) to provide a new and improved method for enterically or intestinally encapsulating pharmaceutical and nutriceutical bioactive agent or agents for oral administration of the encapsulated bioactive agent or agents.

20 Claims, 6 Drawing Sheets

(1)

(2)

MICROENCAPSULATED BIOACTIVE AGENTS FOR ORAL DELIVERY AND METHODS OF USE THEREOF

CROSS-REFERENCE TO RELATED APPLICATIONS

The present application is a continuation of U.S. Ser. No. 12/718,424, filed Mar. 5, 2010, which claims the benefit under 35 U.S.C. 119(e) of U.S. Provisional Application Ser. No. 61/158,231 filed Mar. 6, 2009, the entireties of which are hereby expressly incorporated herein by reference.

U.S. Ser. No. 12/718,424 is also a continuation in part of U.S. Ser. No. 11/938,638, filed Nov. 12, 2007, the entirety of which is hereby expressly incorporated herein by reference.

STATEMENT REGARDING FEDERALLY SPONSORED RESEARCH OR DEVELOPMENT

Not applicable.

BACKGROUND OF THE INVENTION

The presently claimed and disclosed inventive concept(s) relates generally to pharmaceutical and nutriceutical products, and, and more particularly to improved encapsulated pharmaceutical and nutriceutical bioactive agents and methods of their production and methods of their use.

It is often desirable for an orally consumed pharmaceutical or nutriceutical bioactive material to be absorbed into the bloodstream through the wall of the small intestine or large intestine. The delivery vehicle which contains the bioactive agent must be able to pass intact through the stomach and must remain intact in the lumen of the small intestine in order to be passed through the intestinal mucosa and deliver the bioactive agent into the blood stream. Enteric coatings are frequently used to encapsulate oral dosage forms to prevent damage to the active substance contained in the oral preparation by acids and enzymes in the stomach. Enteric coatings are used for example for preventing gastric enzymes from reacting with or destroying the active substance, preventing dilution of the active substance before it reaches the small intestine, ensuring that the active substance is not released until after the preparation has passed the stomach, and preventing damage to the bioactive agent because of the low pH in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

The lumen of the small intestine and the blood vasculature of the intestinal mucosa are ideal dissolution targets for a wide variety of bioactive pharmaceutical and nutriceutical compounds, presuming one is able to overcome its characteristics of impermeability through the intestinal wall. It is to providing such encapsulated pharmaceutical and nutriceutical bioactive materials for optimal delivery to and absorption into the small intestine that the present invention is directed.

SUMMARY OF THE DISCLOSURE

Figure 1:
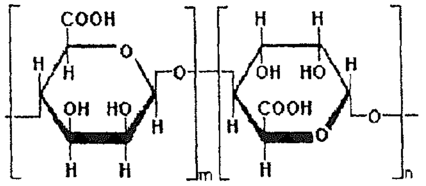
FIG. 1 is a structural representation of the L-guluronic acid (G) and D-mannuronic acid (M) residues which comprise an alginate molecule.

The presently claimed and disclosed inventive concept(s) contemplates a novel oral dosage form (oral delivery vehicle) for the trans-intestinal mucosal delivery of pharmaceutical and nutriceutical bioactive agents (also referred to herein as bioactive compounds). The oral dosage form of the presently claimed and disclosed inventive concept(s) inhibits degradation of the bioactive compound within the stomach and within the lumen of the intestine by encapsulation within a polymeric shell, preventing its dissolution until after passing through the mucosal wall of the small and/or large intestine. The enzymatic degradation of the delivery vehicle containing the bioactive compound is substantially inhibited (resisted) until after absorption of the delivery vehicle into blood vessels of the intestinal mucosa. It is a particular object of the presently claimed and disclosed inventive concept(s) to provide a new and improved method for enterically or intestinally encapsulating pharmaceutical and nutriceutical bioactive agents for oral administration of the encapsulated bioactive agents.

In particular, the presently claimed and disclosed inventive concept(s) relates to the production of a delivery vehicle for oral administration of a protected biologically active (bioactive) agent for subsequent delivery into the small intestine (and more particularly across and into the mucosa thereof) of a mammal. The delivery vehicle bestows protection by encapsulating the bioactive agent, preventing its disintegration and thus dissolution, until the encapsulated agent passes into the mucosal wall of the small intestine into the bloodstream thereof. The bioactive agent is thus preferably protected from enzymatic degradation via the polymeric capsule of the vehicle until after absorption at the intestinal mucosa. The encapsulation formulation of the presently claimed and disclosed inventive concept(s) greatly enhances the bioavailability of bioactive agents via transmucosal delivery enhancing molecules (also referred to herein as transmucosal delivery enhancing agents) extending into and from the polymeric microcapsule of the dosage form which target intestinal mucosa receptors.

DETAILED DESCRIPTION OF THE INVENTION

The description herein of several embodiments describes non-limiting examples that further illustrate the presently claimed invention and disclosed inventive concepts.

In the following detailed description, numerous specific details are set forth in order to provide a more thorough understanding of the disclosure. However, it will be apparent to a person having ordinary skill in the art that the present disclosure may be practiced without these specific details. In other instances, features which are well known to persons of ordinary skill in the art have not been described in detail to avoid complication unnecessarily the description. Therefore, unless defined otherwise, all technical and scientific terms used herein have the same meanings as commonly understood by one skilled in the art to which the presently claimed invention and disclosed inventive concept(s) pertains. For example, the term “plurality” refers to “two or more.” The singular forms “a,” “an,” and “the” include plural referents unless the context clearly indicates otherwise. Thus, for example, reference to “a bioactive agent” refers to 1 or more, 2 or more, 3 or more, 4 or more, or greater numbers of bioactive agents.

The presently claimed and disclosed inventive concept(s) is directed in one embodiment to a process for the encapsulation and subsequent delivery of a water or lipid soluble biologically active agent (bioactive agent) to a mammalian intestinal mucosa, particularly that of humans. The process for forming the delivery vehicle (i.e., the oral dosage form) generally includes the steps of forming an aqueous suspension or oil emulsion (optionally including an emulsifier) of the bioactive (pharmacological or nutriceutical) agent, and encapsulating the suspension or emulsion with a polymeric shell having transmucosal delivery enhancing molecules which are covalently linked to the polymer shell and which extend there from. Preferably the polymeric shell comprises an alginate such as sodium, potassium, or calcium alginate (and optionally contains another polymer such as, but not limited to, carrageenan, xanthan gum, and/or agar-agar) and preferably the transmucosal delivery enhancing molecule comprises isoprenoid or fatty acid “spikes” which are covalently linked to the alginate molecule preferably via carboxyl or hydroxyl groups of the alginate molecule.

Once covalently conjugated as described above, the micro encapsulated bioactive agent may either be solidified through the addition of calcium ions in an atomization process, and thus used in the production of powder-filled capsules or tablets, or the microencapsulated bioactive agent may be left non-solidified and used directly as a wet gel capsule formulation.

The jejunum region of the small intestine in particular is typically a preferred region for disintegration of an oral dosage form of many bioactive materials for two primary reasons. First, the small intestine is specialized for the digestion and subsequent absorption of digestive end products. Second, the small intestine maintains a large surface area conducive to absorption, greatly increasing the probability of drug diffusion therein. Premature disintegration in the stomach, as noted above, exposes many bioactive agents to a potentially degradative environment thereby resulting in an inadequate absorption thereof for therapeutic value. Likewise, dosage disintegration within the large intestine may result in the excretion of a majority of the dosage form as waste, as is the primary function of the colon.

Thus, in one embodiment, the oral dosage form of the presently claimed and disclosed inventive concept(s) is resistant to gastric disintegration, but is readily dissolvable in the lumen small intestine as discussed in more detail below. This embodiment of the oral dosage form comprises an encapsulating formula designed to deliver both water-soluble and lipid soluble drugs intact to the small intestine, particularly the jejunum. Once passing through the duodenum, this embodiment of the delivery vehicle of the presently claimed and disclosed inventive concept(s) readily disintegrates upon contact with digestive enzymes in the small intestine, thereby releasing its solubilized bioactive agent.

More preferably, the presently claimed and disclosed inventive concept(s) relates to the formulation and production of a delivery vehicle containing a water soluble lipid soluble pharmacologically or nutriceutically bioactive agent, for oral delivery and transmucosal passage in the small intestine of a mammal. The presently claimed and disclosed inventive concept(s) preferably comprises the preparation of an emulsion or suspension containing the bioactive agent or agents, and optionally water, glycerin, an emulsifier, propylene glycol or vegetable oil, pH modulator, or protease inhibitor then maintaining the emulsion at a temperature between 0° C. and 150° C. for encapsulation into either a spherical beadlet, biofilm or capsule shell or other dosage form according to methods disclosed herein.

The encapsulation formulations contemplated herein are suitable for the encapsulation and subsequent intestinal delivery of a broad spectrum of hydrophobic and hydrophilic biologically active, therapeutic or nutritionally-useful molecules such as, but not limited to, those described elsewhere herein.

Pharmacological bioactive agents which may be contained within the delivery vehicle of the presently claimed and disclosed inventive concept(s) generally include, but are not limited to, antibiotics, antiviral agents, anti-inflammatory agents, anti-tumor agents, polypeptides, steroidal agents, anti-sense agent, RNA agents and DNA agents. Nutriceutical bioactive agents which may be used include, but are not limited to, carotenoids, vitamins, minerals, phototropic agents and anthocyanins.

An initial step in the process of the presently claimed and disclosed inventive concept(s) comprises suspending or emulsifying the bioactive agent in one or more types of water or oil bases, optionally with a thickener or stabilizer, and a pH modulator or protease inhibitor, or any combination thereof.

Any combination of the following pharmaceutical grade reagents may be used, for example, for a water emulsion of the bioactive agent; distilled deionized water, glycerin, Tween™, propylene glycol, or any other of a number of suitable water soluble mediums. Any combination of pharmaceutical grade oils from the following list may be suitable to form an oil emulsion where desired, including but not limited to, soybean oil, peanut oil, sesame oil, safflower oil, canola oil, cotton seed oil, olive oil, corn oil and/or vegetable oil or other oils from vegetable materials.

As noted herein, the suspension or emulsion preferably comprises a thickener or stabilizer such as a gum, resin, or gum-resin. Among the suitable gums, resins, and gum-resins which may be used alone or in combination include, but are not limited to, cellulose gum, pectin and its resins, locust bean gum, resins and derivatives, xanthan gum and resins, carrageenan and derivatives, sodium salt of carrageenan, gellan gum and resins, whey protein gum and resins, agar agar, propylene glycol, alginate derivatives and resins, gum Arabic and resins, guar gum and resins, gum tragacanth, and gum ghatti. Gums are understood herein to comprise water-soluble materials while resins are soluble in non-aqueous solvents or oils.

The emulsion may comprise an emulsifier such as Tween 20®, or others known in the art. Examples of emulsifiers which may be used include but are not limited to non-ionic, anionic, cationic and amphoteric surfactants such as are commercially available, for example from Sigma Aldrich Co. Specific examples include, but are not limited to, 2-Cyclohexylethyl β-D-maltoside, Brij 30®, Brij 56®, Brij 72®, Decyl β-D-maltopyranoside, Diethylene glycol monodecyl ether, Diethylene glycol monohexadecyl ether, Diethylene glycol monopentyl ether, Ethylene glycol monodecyl ether, Ethylene glycol monohexadecyl ether, Heptaethylene glycol monododecyl ether, N-Decanoyl-N-methylglucamine, N-Nonanoyl-N-methylglucamine, N-Octanoyl-β-D-glucosylamine, Nonyl β-D-glucopyranoside, Octaethylene glycol monodecyl ether, Octaethylene glycol monohexadecyl ether, Pentaethylene glycol monodecyl ether, Polyoxyethylene 10 tridecyl ether, Polyoxyethylene 20 oleyl ether, Polyoxyethylene 40 stearate, Pril neutral Detergent®, Saponin, Span 20®, Span 60®, Span 80®, Sucrose monodecanoate, Sucrose monolaurate, TWEEN 20®, TWEEN 40®, TWEEN 80®, TWEEN 85®, Tergitol NP-9®, Tergitol TMN 10®, Tergitol®, Tergitol Type 15-S-12®, Tetraethylene glycol monodecyl ether, Tetraethylene glycol monohexadecyl ether, Tetraethylene glycol monooctadecyl ether, Tetramethylammonium hydroxide pentahydrate, Triethylene glycol monodecyl ether, Triethylene glycol monooctadecyl ether, Triton®, Triton N-60®, Triton X-100®, Triton X-102®, Triton X-15®, Triton X-207®, Triton X-45®, Triton XL-80N®, Tyloxapol, Undecyl-β-D-maltoside, n-Dodecyl β-D-maltoside, 1-Octanesulfonic acid sodium salt, Chenodeoxycholic acid, Cholic acid, Dehydrocholic acid, Deoxycholic acid, Glycocholic acid hydrate, Lithium dodecyl sulfate, N,N-Dimethyldodecylamine N-oxide solution, N-Lauroylsarcosine sodium, Niaproof 4®, Sodium 1-butanesulfonate, Sodium 1-decanesulfonate, Sodium 1-dodecanesulfonate, Sodium 1-heptanesulfonate, Sodium 1-nonanesulfonate, Sodium 1-propanesulfonate, Sodium cholate, Sodium choleate, Sodium deoxycholate monohydrate, Sodium dodecyl sulfate, Sodium dodecylbenzenesulfonate, Sodium glycodeoxycholate, Sodium hexanesulfonate, Sodium octyl sulfate, Sodium pentanesulfonate, Sodium taurochenodeoxycholate, Triton QS-15®, Triton QS-44®, Triton X-200®, Triton XQS-20®, Trizma dodecyl Sulfate®, Ursodeoxycholic acid, Alkyltrimethylammonium bromide, Amprolium hydrochloride, Benzalkonium chloride, Benzethonium chloride, Benzyldimethylhexadecylammonium, Choline p-toluenesulfonate, Denatonium benzoate, Dimethyldioctadecylammonium bromide, Ethylhexadecyldimethylammonium bromide, Hexadecylpyridinium bromide, Hexadecyltrimethylammonium bromide, Hyamine 1622®, Luviquat FC 370®, Luviquat HM 552®, Methylbenzethonium chloride, Tetraheptylammonium bromide, Tetrakis(decyl)ammonium bromide, 3-[N,N-Dimethyl(3-palmitoylaminopropyl)ammonio]-propanesulfonate, ASB-14, EMPIGEN BB Detergent®, N-Dodecyl-N,N-dimethyl-3-ammonio-1-propanesulfonate, and Sodium 2,3-dimercaptopropanesulfonate monohydrate.

Other compounds which may be added include, but are not limited to, glycyrrhizinate, glycyrrhizinic acid, sucrose fatty acid ester, glycerin, glycerol fatty acid ester, adipic acid, polyethylene glycol, sodium dodecyl sulfate, sodium caprate, and sodium deoxycholate, sodium chloride, potassium chloride, calcium chloride or any combination thereof.

The delivery vehicle, in a preferred embodiment of the presently claimed and disclosed inventive concept(s), includes a transmucosal delivery enhancing molecule, which may be, but is not limited to, (1) medium or long chain fatty acids such as linoleic acid, (2) isoprenoids, (3) vitamins or (4) signal peptides. The transmucosal delivery enhancing molecules may be added in combination (i.e. various compounds) or individually (i.e. a single compound). The dosage form contemplated herein may comprise a pH modulating agent, as noted above. For example, an acid (e.g., citric acid) may be added as the pH modulator to lower the local intestinal luminal pH upon disintegration of the delivery vehicle and release of the bioactive agent. Although any of a number of acids (such as fruit acids including lactic acid, malic acid, alpha hydroxy acids, glycolic acid, and citric acid) could be used for this purpose, citric acid is preferred at a level of around 0.006 g/kg. A pH modulator provides the benefit of reversible pH inhibition of intestinal luminal enzymatic activity thus mitigating bioactive agent cleavage prior to absorption within the intestine.

Examples of isoprenoid-type transmucosal delivery enhancing molecules used herein include, but are not limited to, lycopene, limonene, gamma-tocotrienol, geraniol, carvone, farnesol, geranylgeraniol, squalene, and other linear terpenoids, carotenoids, taxol, vitamin E, vitamin A, beta-carotene, Coenzyme $Q_{10}$ (ubiquinone), astaxanthin, zeaxanthin, lutein, citranxanthin, beta-choro-carotene, and canthraxanthan.

Transmucosal delivery enhancing molecules for use within the presently claimed and disclosed inventive concept(s) also include long and medium chain fatty acids, including linoleic acid, myristic acid, palmitic acid, for example, and generally fatty acids with a chain length varying from 6-28 carbon atoms. For use within the methods of the presently claimed and disclosed inventive concept(s), long chain fatty acids, especially fusogenic lipids (unsaturated fatty acids and monoglycerides such as oleic acid, linolenic acid, linoleic acid, monoolein, phosphatidylserine, and phosphatidylethanolamine) provide useful carriers to enhance transmucosal delivery of the bioactive agents contemplated herein. Medium chain fatty acids (C6 to C12) and may also be used to enhance transmucosal delivery of the vehicle of the presently claimed and disclosed inventive concept(s). Other medium and long chain fatty acids that can be used as translocation enhancers herein include, but are not limited to myristoleic acid, palmitoleic acid, oleic acid, alpha-linolenic acid, arachidonic acid, eicosapentaenoic acid, erucic acid, and docasahexaenoic acid. Examples of naturally-occurring fatty acids which may be used in the presently claimed and disclosed inventive concept(s) include but are not limited to C8:0 (caprylic acid), C10:0 (capric acid), C12:0 (lauric acid), C14:0 (myristic acid), C16:0 (palmitic acid), C16:1 (palmitoleic acid), C16:2, C18:0 (stearic acid), C18:1 (oleic acid), C18:1-7 (vaccenic), C18:2-6 (linoleic acid), C18:3-3 (alpha-linolenic acid), C18:3-5 (eleostearic), C18:3-6 (delta-linolenic acid), C18:4-3, C20:1 (gondoic acid), C20:2-6, C20:3-6 (dihomo-gamma-linolenic acid), C20:4-3, C20:4-6 (arachidonic acid), C20:5-3 (eicosapentaenoic acid), C22:1 (docosenoic acid), C22:4-6 (docosatetraenoic acid), C22:5-6 (docosapentaenoic acid), C22:5-3 (docosapentaenoic), C22:6-3 (docosahexaenoic acid) and C24:1-9 (nervonic). Highly preferred unbranched, naturally occurring fatty acids are those with from 14 to 22 carbon atoms. In addition, sodium salts of medium and long chain fatty acids are effective transmucosal delivery enhancing molecules. Transmucosal delivery enhancing molecules contemplated herein also include signal peptides.

A protease inhibitor may be included in the delivery vehicle contemplated herein as well. Examples of such protease inhibitors include, but are not limited to, AEBSF-HCI, Amastatin-HCI, (epsilon)-Aminocaproic acid, (alpha)1-Antichymotrypsin from human plasma, Antipain-HCL, Antithrombin III from human plasma, (alpha)1-Antitrypsin from human plasma, (4-Amidinophenyl-methane sulfonyl-fluoride), Aprotinin, Arphamenine A, Arphamenine B, Benzamidine-HCI, Bestatin-HCI, CA-074, CA-074-Me, Calpain Inhibitor I, Calpain Inhibitor II, Cathepsin Inhibitor Z-Phe-Gly-NHO-Bz-pMe, Chymostatin, DFP (Diisopropylfluorophosphate), Dipeptidylpeptidase IV Inhibitor H-Glu-(NHO-Bz)Pyr, Diprotin A, E-64, E-64d (EST), Ebelactone A, Ebelactone B, EDTA-Na2, EGTA, Elastatinal, Hirudin, Leuhistin, Leupeptin-hemisulfate, (alpha)2-Macroglobulin from human plasma, 4-(2-Aminoethyl)-benzenesulfonyl fluoride hydrochloride, Pepstatin A, Phebestin, Phenylmethyl sulfonyl fluoride, Phosphoramidon, (1-Chloro-3-tosylamido-7-amino-2-heptanone HCI, (1-Chloro-3-tosylamido-4-phenyl-2-butanone), Trypsin inhibitor from egg white (Ovomucoid), and Trypsin inhibitor from soybean.

The emulsion or suspension used in the presently claimed and disclosed inventive concept(s) may also contain small quantities of butylated hydroxy toluene, glycerine, polyethylene glycols, propylene glycol, lecithin, antioxidants, tocopherol, docosahexaenoic acid, and pirotiodecane in addition to coloring agents, solubilizers and extenders.

The aqueous and/or oil emulsion or suspension may further comprise a pharmaceutically acceptable solid or liquid filler or diluent. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials such as known to persons of ordinary skill in the art. A tabulation of ingredients listed by the above categories can be found in the U.S. Pharmacopeia National Formulary, 1990, pp. 1857-1859 which is incorporated herein by reference in its entirety. Some examples of the materials which can serve as pharmaceutically acceptable carriers of the bioactive agents include but are not limited to sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; pyrogen-free water; isotonic saline; Ringer's solution, ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of active ingredient that can be combined with the carrier materials to produce a single dosage form will vary depending upon the particular mode of administration.

The emulsions or suspensions of the presently claimed and disclosed inventive concept(s) may be prepared by methods known to those of ordinary skill in the art. In one non-limiting method, a combination of appropriate water or oil base, depending on the chemical characteristics of the bioactive agent, are combined with bioactive agent at a rate of, for example, 5-100 times the bioactive weight amount. For example, a typical antibiotic, e.g., cephalosporin, can be emulsified within Tween 20® with a small added amount of glycerin. Next, a polymeric encapsulating material as described herein can be added in combination with a translocation delivery enhancing molecule, such as linoleic acid or an isoprenoid such as lycopene or other compounds as described and contemplated herein. A pH modulator optionally can be added as well. This mixture can then be vortexed or sonicated or otherwise combined for some period of time at a temperature ranging from 0-28° C. A stabilizer such as a gum (such as xanthan gum), may be added. The emulsion or suspension of the bioactive agent can then be encapsulated within the biofilm polymeric outer membrane of the invention by any of a number of possible processes such as, but not limited to, those described herein.

The encapsulated bio-active agent material is preferably cured to a moisture (water) content ranging from <0.01-5% depending upon the transmucosal delivery site and bioactive agent for encapsulation. Colorants or vitamin or mineral enhancers may be added to the capsule membrane as well.

A powder form of a bioactive agent may be encapsulated in another example of an intestinal delivery membrane by a further process of the presently claimed and disclosed inventive concept(s). For example, an emulsion of agar agar, glycerin, carrageenan, sugar and water can be homogenized to a gel as described above for the standard gel polymer, however here the gel polymer would be molded and cured in a manner allowing for the preparation of a capsule shell which could be pulled apart for the packaging of a bioactive powder and then its two parts put back together producing a viable intestinal targeting disintegration tablet. In one embodiment the encapsulated bioactive agent can be disposed in a gel cap or capsule shell and/or poured or molded in a manner for the formation of a thin sheet or biofilm for processing into small cube sheets about 0.5 square inches for the delivery of its bioactive agent in the mammalian mouth whether on top of the tongue, under, or between the cheek and gums. Various methods exist in the art which may be used in the practice of the presently claimed and disclosed inventive concept(s) to introduce the bioactive emulsion into either liquid, gel, solid or film form. The final bioactive micro-beadlets, gel caps, capsules or biofilm delivery vehicles may then be packaged within a number of suitable containment systems for shelf storage prior to the oral administration to the mammalian subject.

For many years scientists have sought a vehicle for the oral transport of therapeutic agents within the mammalian system. As noted above, the desire has always been to transport a drug to the most effective medium for therapeutic disposition into the blood serum. Generally most oral drug or bioactive delivery systems transport their active agent to either or both of the gastric or intestinal fluids. However, there are many shortcomings with this approach. First, many existing oral vehicles must be loaded with medicinal or therapeutic doses far in excess of those required for effective therapy because of the premature disintegration in gastric or intestinal fluids where the acidic or enzymatic environments may cause degradation of some portion or all of the bioactive molecule. In other cases therapeutic dose loss is due to loss through the large intestine as a waste product serum. Usually some combination of all of these is at play. Secondly, traditional systems are limited in the type and size of molecule they can effectively transport to the bloodstream via the oral route. For example, it may be expected that a very small molecule such as the antibiotic ceftriaxone sodium (molecular formula $C_{18}H_{16}N_8Na_2O_7S_3$) could easily be absorbed via oral delivery. However, this is not the case, many have tried this unsuccessfully and thus this antibiotic may only be given intravenously or intramuscularly. This is due to the lack of a molecular mechanism of transport for the molecule across the phospholipid bilayer of the intestinal mucosal cells.

The mechanisms of transmucosal transfer are generally limited to passive diffusion, facilitated passive diffusion, active transport and pinocytosis or some combination thereof. As is the case with ceftriaxone, for many therapeutic agents these molecular limitations are far too difficult to overcome. On the other hand, one may consider uptake of much larger molecules such as proteins such as insulin. Insulin is subjected to significant gastric degradation when using conventional oral delivery systems and there is a high degree of inhibition to mucosal uptake. Presently, effective oral vehicles for the protective transport and disposition directly into the bloodstream of therapeutic proteins, DNA, or RNA are not available.

The presently claimed and disclosed inventive concept(s) thus constitutes a novel oral delivery vehicle able to protect its contents from degradation during its passage through both the gastric and intestinal fluids and through the intestinal mucosa for disposition within the blood serum thereof.

Without being bound by theory, it is believed that the transmucosal delivery enhancing molecules (e.g., isoprenoids or fatty acids) which coat and extend from the encapsulation polymeric shell in the presently claimed and disclosed inventive concept(s) become encapsulated by intestinal lipids in the intestine, enabling the encapsulated bioactive agent to be taken up through the intestinal mucosa without first being degraded within the lumen of the intestine. Furthermore, rather than protruding solely as "spikes" on the surface of the encapsulation shell, some portion of the transmucosal delivery enhancing molecules (e.g., the isoprenoid or fatty acid groups) are internalized within the core of the polymer shell of the dosage form making it substantially resistant to disintegration by both gastric and intestinal fluids and enzymes. Further analysis indicated that the oral delivery vehicle of the presently claimed and disclosed inventive concept(s) substantially releases the encapsulated bioactive agent within the blood serum within 15 minutes after deposition therein. Experiments using encapsulated methylene blue within the transport system of the presently claimed and disclosed inventive concept(s) showed zero disintegration within gastric and intestinal fluids, and 100% disintegration within 15 minutes of entering blood serum through the intestinal mucosa.

In preferred embodiments of the presently claimed and disclosed inventive concept(s), calcium alginate (obtained for example by reaction of sodium alginate with a calcium salt such as $CaCl_2$) is the primary polymer base or "backbone" of the shell of the oral delivery vehicle. In the configuration contemplated herein it forms multiple cross-linked helix-helix aggregates as explained below resulting in superior encapsulation strength. In alternative embodiments, a minor portion of the shell comprising calcium alginate (and/or other polymers contemplated herein) further comprises quantities of one or more other natural gums for cross-linking and thickening, such as, but not limited to, carrageenan, agar agar, guar gum and/or xanthan gum. The polymeric shell component of the delivery vehicle is initially made using sodium alginate (or potassium alginate) as the polymer base building block which is then, in one embodiment, converted to a more stable calcium form through ionic exchange as described below. The exchange of sodium (or potassium) by calcium particularly enhances multiple cross-linkage formation between molecules of alginate enabling precipitation. The alginate portion preferably ranges from 5%-99.5% by weight in the final oral dosage form while the other gums (e.g., carrageenan, agar-agar, guar gum or xanthan gum), may optionally make up 0.1-5% of the final dosage form. In other embodiments of the presently claimed and disclosed inventive concept(s), the sodium (or potassium) alginate is left in a gel form rather than in a precipitated form. The sodium, potassium, or calcium alginate polymer used, as above, may have a molecular weight ranging from 10,000-600,000 daltons, or preferably 100,000-400,000 daltons, or more preferably 300,000-320,000 daltons, and still more preferably 305,000 daltons.

Figure 2:
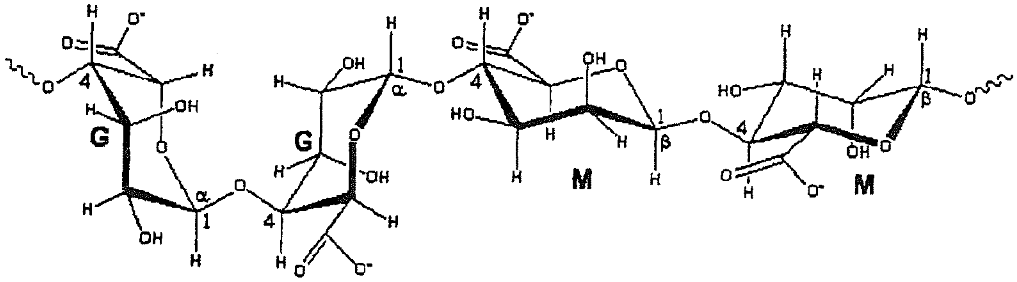
FIG. 2 is a structural representation of an alginate molecule having repeating alternate guluronic and mannuronic dimer units.

Sodium alginate is typically obtained by extraction from brown algae and is widely used within the food industry to increase product viscosity and as an emulsifying agent. Sodium alginate has an empirical formula of $NaC_6H_7O_6$ having a molecular structure as shown in FIGS. 1 and 2. Alginates are linear unbranched polymers containing β-(1→4)-linked D-mannuronic acid (M) and its epimer α-(1→4)-linked L-guluronic acid (G). D-mannuronic acid residues are enzymatically converted to L-guluronic after polymerization.

Alginates are not random copolymers but, according to the algal source, comprise blocks of similar alternating residues, each of which have different conformational preferences and behavior. The alginate polymer may comprise, for example, homopolymeric blocks of consecutive G-residues, or consecutive M-residues, or alternating M- and G-residues or randomly organized blocks of G- and M-residues. For example, the M/G ratio of alginate from *Macrocystis pyrifera* is about 1.6 whereas that from *Laminaria hyperborea* is about 0.45.

As noted, the encapsulation shell of the oral dosage form of the presently claimed and disclosed inventive concept(s) may comprise amounts of other carbohydrate gum polymers, which cause thickening and/or cross-linking of the alginate molecules including carrageenan, xanthan gum, guar gum, and agar agar as described below.

Figure 3:
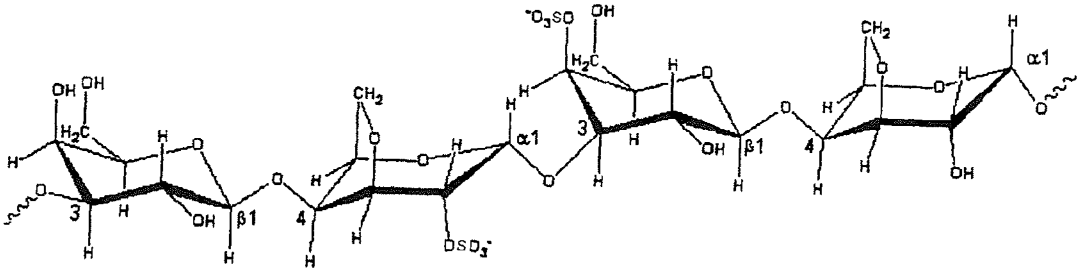
FIG. 3 is a structural representation of a carrageenan molecule.

Carrageenan is a generic term for several polysaccharides extracted from a type of red seaweed, which is abundant along the Irish coastline. Carrageenan differs from agar in that it has have sulfate groups (—$OSO_3$) in place of certain hydroxyl groups. Carrageenans are linear polymers of about 25,000 galactose derivatives with regular but imprecise structures, dependent on the source and extraction conditions. More specifically, Carrageenan consists of alternating 3-linked-β-D-galactopyranose and 4-linked-α-D-galactopyranose units. Carrageenan is a large highly flexible molecule which coils forming a helical structure, giving the molecule the ability to form a variety of different gels at room temperature. Carrageenan is used primarily within the food industry as a thickening and stabilizing agent. In one example, Carrageenan has the molecular structure shown in FIG. 3.

Figure 4:
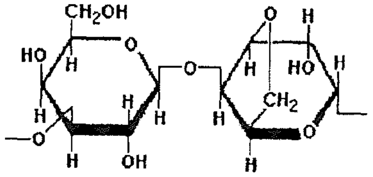
FIG. 4 is a structural representation of the repeating agarabiose dimer unit of agar agar.

Agar-agar is extracted from the cell membranes of some species of red algae, particularly those from the genera *Gelidium* and *Gracilaria*. Historically agar-agar has chiefly been used as an ingredient in desserts, especially in Japan. Agar-agar comprises a mixture of agarose and agaropectin. Agarose is a linear polymer, of molecular weight about 120,000, based on the -(1->3)-β-D-galactopyranose-(1->4)-3,6-anhydro-α-L-galactopyranose unit, the major differences from carrageenans being the presence of L-3,6-anhydro-α-galactopyranose rather than D-3,6-anhydro-α-galactopyranose units and the lack of sulfate groups. Agaropectin is a heterogeneous mixture of smaller molecules that occur in lesser amounts. Their structures are similar but slightly branched and sulfated, and they may have methyl and pyruvic acid ketal substituents. The molecular structure of agarabiose disaccharide units is shown in FIG. 4.

Figure 5:
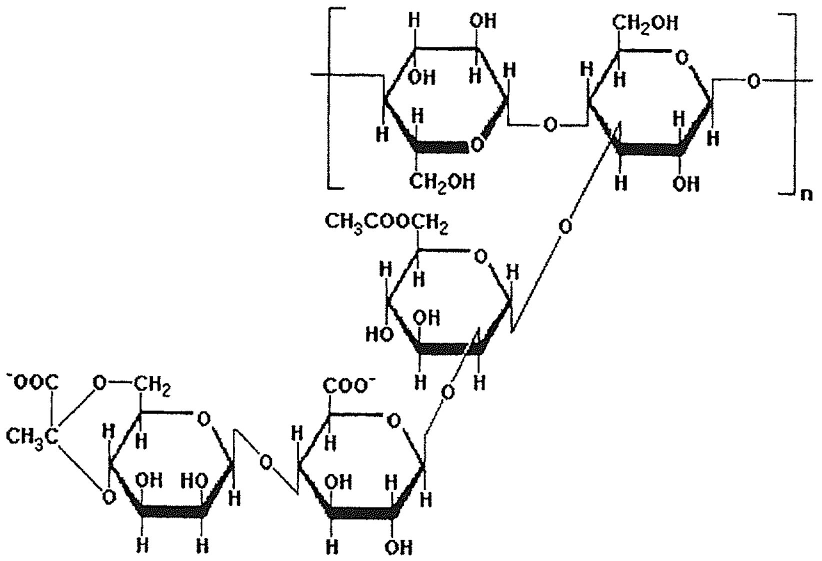
FIG. 5 is a structural representation of the repeating unit of xanthan gum.

Xanthan gum is prepared through an aerobic submerged fermentation from *Xanthomonas campestris*. Xanthan gum has a β-D-glucose backbone like cellulose, but every second glucose unit is attached to a trisaccharide comprising of mannose, glucuronic acid, and mannose. The mannose closest to the backbone has an acetic acid ester on carbon 6, and the mannose at the end of the trisaccharide is linked through carbons 6 and 4 to the second carbon of pyruvic acid. This polysaccharide is used as a food additive primarily for product thickening and dispersion. Xanthan gum has the molecular structure shown in FIG. 5.

Figure 6:
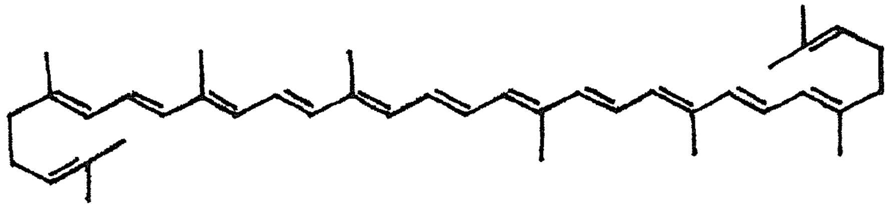
FIG. 6 is a structural representation of lycopene.
Figure 7:
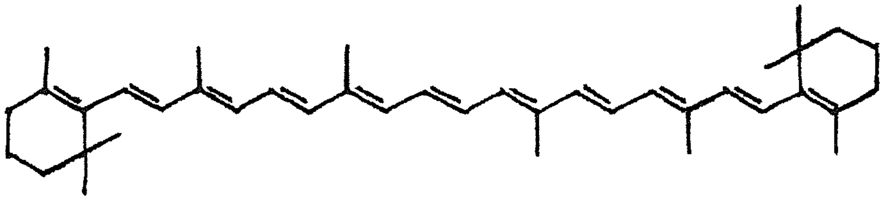
FIG. 7 is a structural representation of beta-carotene.

Lycopene is an isoprenoid pigment responsible for the bright red color of tomatoes and other red fruits and vegetables. As a carotene, lycopene is an important intermediate in the biosynthesis of many carotenoids, such as a beta carotene. Lycopene is a symmetrical tetraterpene assembled from 8 isoprene units (FIG. 6). Beta-carotene, another isoprenoid compound used herein as a transmucosal delivery enhancer, is shown in FIG. 7.

Figure 8:
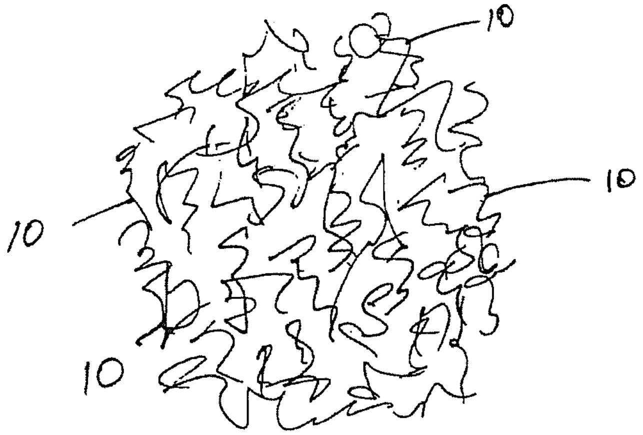
FIG. 8 is a representation of an aqueous sodium alginate gel.

Sodium alginate (and potassium alginate) has the unusual ability to form a gel upon agitation within cold water which will not solidify upon standing (represented schematically in FIG. 8). The gels thus formed have a high encapsulation affinity, meaning the ability of the alginate molecule to surround and wind itself around another molecule (represented schematically in FIG. 9). The alginate polymer is able to encapsulate many classes or types of molecules, including, but not limited to, therapeutic or nutraceutic agents such as antibiotics, antivirals, oncological agents, anti-lipids, antihypertensives, cardiac drugs, antidiabetic agents, vitamins, minerals, proteins, peptidomimics, and RNA or DNA molecules. More specifically the encapsulated bioactive agent of the present ly claimed and disclosed inventive concept(s) may be selected, for example, from anabolic agents (e.g., boldandiol, ethylestrenol, mibolerone, nandrolone, oxymetholone, stanozol, and testosterone); antibacterial/antibiotics (e.g., aminoglycosides including: amikacin, apramycin, dihydrostreptomycin, gentamicin, kanamycin, neomycin, spectinomycin, vancomycin; cephalosporins including: cefaclor, ceftazidime, cephalexin, cephalothin; clindamycin; chlorhexidine, fatty acid monoesters, such as glycerol monolaurate; fluoroquinolones including enroflaxacin, ciprofloxacin; macrolides including erythromycin, lincomycin, tylosin; penicillins including amoxicillin with and without potentiators, ampicillin, hetacillin, ticarcillin; tetracycline and analogues; sulfanomides with or without potentiators including sulfachlorpyridazine, sulfadimethoxine, sulfamethazine, and sulfaquinoxaline); antifungals (e.g., miconazle, itraconazle, griseofulvin, glycerol mono-laureate, and metronidazole); anti-cancer agents (e.g., actinomycin-D, cisplatin, cytarabine, doxorubicin, 5-fluorouracil, methotrexate, pergolide, purine analogues, oncovin, vinblastine, and vincristine); antidotes and reversing agents (e.g., atropine, 2-PAM, naloxone, and nalorphineHCl, yohimbine, (atipamazole); antihistamines (e.g., cromolyn sodium, diphenhydramine, pyrilamine, and tripelennamine); antipyretics (e.g. acetaminophen); non-steroidal anti-inflammatory drugs (NSAIDs), (e.g., flunixin meglumine, acetylsalicylic acid, ibuprofen, ketoprophen, meclofenamic acid, naproxen, phenylbutazone, and zileutin); steroidal anti-inflammatory drugs (e.g., beclomethasone, budesonide, dexamethasone, flumethasone, flunisolide, fluticasone, isoflupredone, prednisolone, and triamcinolone); anti-thrombotics (e.g., acetylsalicylic acid); anti-tussives (e.g., narcotic analgesics, dextromethorphan, and phlocodine); bronchodilators (e.g., atropine, albuterol, clenbuterol, pirbuterol, salmeterol, fenoterol, aminophylline, glycopyrrolate, terbutaline, and theophylline); parasympathomimetics (e.g., bethanechol); anticholinergics (e.g., atropine, ipratropium, and tiotropium); anti-virals (e.g. pyrimidine nucleosides including idoxyuridine, and trifluridine; purine nucleosides including: vidarabine, and acyclovir; ribaviran, amantadine, interferon and its inducers, and other miscellaneous anti-virals, for example, thiosemicarbazones, zidovine, and benzimidazoles); sympathomimetics (e.g., epinephrine); cardiovascular agents (e.g., calcium channel blockers: diltiazem, nifedipine, and verapamil); anti-arrhythmics (e.g., alprenolol, amiodarone, bretylium, diltiazem, flecainide, isoproteronol, lidocaine, metoprolol, nadolol, procainamide, propranolol, quinidine, timolol, and verapamil); vasoactive drugs (e.g., caprotil, epinephrine, hydralazine, isoxsuprine, nitroglycerin, pentoxyfylline, phentolamine, and prazosin); cardiotonics (e.g., dobutamine; dopamine; digitoxin; and digoxin); central nervous agents: e.g., anesthetics including barbiturates; anticonvulsants e.g., clonazepam, diphenylhydantoin, primidone; antidepressants: e.g., SSRI (selective serotonin re-uptake inhibitor); antiemetics: e.g., domperidone, metoclopramide; emetics: apomorphine; narcotic analgesics: codeine, demerol, fentanyl, hydrocodone, meperidine, morphine, oxymorphone, butorphanol, buprenorphin pentazocine; non-narcotic analgesics including acetominophen, aspirin, dipyrone; respiratory stimulants: e.g., caffeine, doxapram, zolazepam; sedatives/tranquilizers including: barbiturates; alpha 2 antagonists (e.g., detomidine, medetomidine, dexmedetomidine, carfentanyl, diazepam, droperidol, ketamine, midazolam, phenothiazine tranquilizers (including acepromazine, chlorpromazine, ethylisobutrazine, promazine, and trifluromazine), romifidine, xylazine; diuretics (e.g., chlorthiazide, and furosemide); dental hygiene (e.g., glycerol monolaurate materials and orally active antibiotics); gastrointestinal agent (e.g., cimetidine ($H_2$ agonist), famotidine, ranitidine, and omeprazole); hypotensives (e.g., acepromazine, and phenoxybenzamine); hormones (e.g., ACTH, altrenogest, estradiol 17beta, estrogens GNRH, FSH, LH, insulin, LHRH, megestrol, melatonin, misoprostol, norgestomet, progesterone, testosterone, thyroxine, and trenobolone); immunomodulators (stimulants including: levamisole, imiquimod and analogues, biological derivative products; and suppressants including: azathioprine); internal parasiticides (e.g., ivermectin, mebendazole, monensin, morantel, moxidectin, oxfendazole, piperazine, praziquantel, and thiabendazole); miotics (e.g. acetylcholine, carbachol, pilocarpine, physotigmine, isofluorophate, echothiophate, and prolidoxime); mydriatics (e.g., epinephrine, and phenylephrine); mydriatics/cycloplegics (e.g. atropine, scopalamine, cyclopentolate, tropicamide, and oxyphenonium); prostaglandins (e.g., cloprostenol, dinoprost tromethamine, fenprostalene, and fluprostenol); muscle relaxants (e.g., aminopentamide, chlorphenesin carbamate, methocarbamol, phenazopyridine, and tiletamine); smooth muscle stimulants (e.g., neostigmine, oxytocin, and propantheline); serotonin; urinary acidifiers (e.g., ammonium chloride, ascorbic acid, and methionine); and vitamins/minerals (e.g., Vitamins A, B, C, D, K, and E).

Although sodium alginate (or potassium alginate) in itself is very effective in molecular encapsulation activity, an even higher encapsulation affinity to the bioactive agent therein can be obtained through the addition of 0.1 to 1% to 2% to 3% to 4% to 5% or more of a thickening agent or cross-linking agent such as carrageenan, xanthan gum, and/or agar-agar to the alginate. In this way a three-dimensional network builds up in which double helices form junction points of the polymer chains thus allowing for the formation of multiple helix-helix aggregates which wind around the bioactive agent.

The helix-helix aggregates thus formed, although very effective in their ability to fully encapsulate and protect the bioactive agent, are not capable of transporting the bioactive agent intact through both the gastric and intestinal fluids for direct transmucosal transport disposition through the intestinal mucosa into the blood serum. This is due to the fact that in the gel state the sodium alginate encapsulation shell is in a water soluble form. To form a stable, insoluble, enterically-resistant, oral dosage form, the helix-helix aggregates which securely encase the bioactive agent, must next be converted to an insoluble state. This is done through ionic exchange. For example, upon dispersion of the sodium alginate aggregates within an aqueous solution of calcium chloride (e.g., 2% to 40% by weight, preferably 5-24% or any effective concentration) or calcium acetate or aluminum sulfate for example, the sodium (or potassium) of the alginate aggregates is replaced by calcium. This reaction occurs rapidly at room temperature (e.g., 20-25° C.) or below resulting in the formation of helix-helix loaded aggregates which rapidly separate from the aqueous medium in the form of a rubbery powder precipitate. The resulting aggregate powder is then dried to a moisture content of <5%, and preferably <1%, forming an encapsulated product which is substantially 100% resistant to gastric fluid (i.e., enterically resistant) but is still extremely susceptible to intestinal disintegration. In fact, in this state the encapsulated aggregates typically break down within 15 minutes upon entering the intestinal pool thus releasing 100% of the bioactive agent. This system in itself is a valuable transport vehicle for those therapeutic agents requiring intestinal disposition for example, probiotics (microorganisms) and vaccines.

In addition to converting loaded aggregates to a water-insoluble form, calcium plays another key role in the molecular configuration of the oral dosage form. In particular, it causes cross-linkage of neighboring polymer molecules through calcium cross-linking. The resulting stability of the delivery system is set in a three dimensional substantially-spherical configuration which serves not only to hold microorganisms or bioactive agents more securely, but in the protection of the bioactive or microorganism from oxidative degradation, UV degradation, moisture degradation in addition to a vast number of other environmental stresses.

However, those bioactive agents whose optimal benefit would be achieved through direct disposition within the blood stream require an additional component capable of enabling transmucosal delivery of the dosage form into the blood serum of a patient through a naturally occurring transport gateway. This is accomplished in the presently claimed and disclosed inventive concept(s) by incorporation of a transmucosal delivery enhancing molecule comprising one or more fatty acids, isoprenoid compounds, vitamins, signal peptides, or other molecules capable of interacting with the natural lipids present in the intestinal pool or mucosa or with any of a number of bilayer transport proteins and/or systems. Preferably, the transmucosal delivery enhancing molecules are covalently linked to the alginate backbone of the transport system thereby protruding from the surface of the dosage form as a "spike" capable of interacting with the natural lipid uptake mechanism responsible for the transmucosal transport of lipids into the blood serum.

Figure 9:
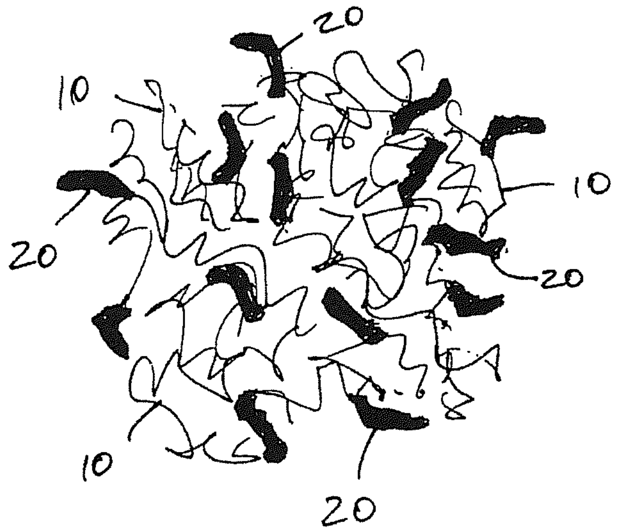
FIG. 9 is a representation of the sodium alginate gel of FIG. 8 combined with transmucosal delivery enhancing molecules.
Figure 10:
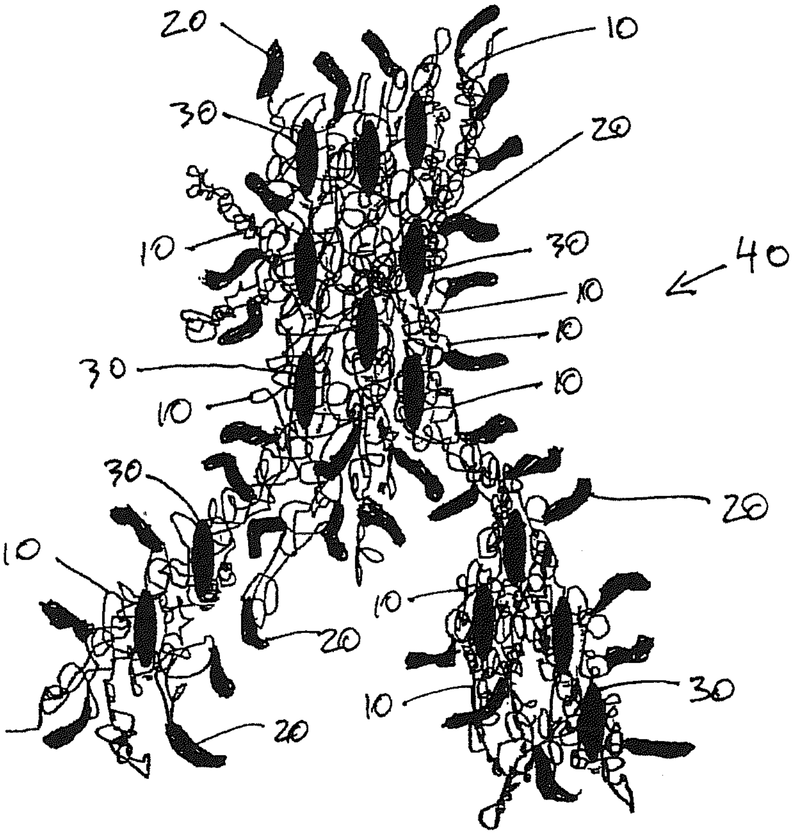
FIG. 10 is a representation of the enhanced gel aggregates of FIG. 9 sodium alginate molecules have been mixed with a bioactive agent encapsulated by the enhanced soluble alginate gel.
Figure 11:
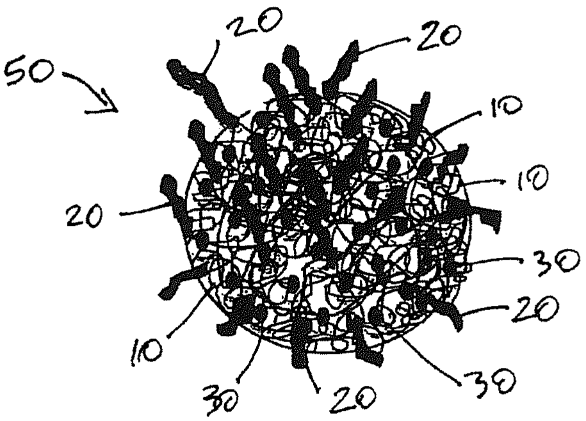
FIG. 11 is a representation of the encapsulated bioactive agent-gel aggregates of FIG. 10 which have been converted to a solidified delivery vehicle by exposure to a calcium source.

Shown in FIG. 8 is a representation of an alginate comprising alginate molecules 10 in gel form, prior to treatment. FIGS. 9, 10 and 11 show representations of various stages of the components of the bioactive agent transport vehicles comprising transmucosal delivery "spikes" thereon.

Shown in FIG. 9 is a representation of the alginate gel of FIG. 8 after it has been mixed with a transmucosal delivery enhancing molecule, for example an isoprenoid such as beta-carotene or lycopene, or a fatty acid such as linoleic acid to form an enhanced alginate mixture. The transmucosal delivery enhancing molecules 20 become covalently conjugated to the alginate molecules 10, such as via carboxyl or hydroxyl groups thereof and form "spikes" (represented as "20" in FIG. 9) which extend from the enhanced alginate gel. Another aggregating enhancing polymer may also be added to this enhanced alginate composition such as described above, for example carrageenan, xanthan gum, or agar agar. The enhanced alginate gel of FIG. 9 is then combined and mixed with the bioactive agent 30 desired to be encapsulated to form the soluble gel encapsulated bioactive agent 40 in one embodiment of the dosage form of the presently claimed and disclosed inventive concept(s), which exists in a water soluble gel form as shown in FIG. 10. In one embodiment of the presently claimed or disclosed inventive concept(s), this gel form is enclosed within a capsule for oral consumption and passage of the bioactive agent 30 through the stomach to the small intestine.

Alternatively, in a preferred version of the presently claimed and disclosed inventive concept(s), and as discussed in further detail below by way of example, the encapsulated bioactive agent formed from the enhanced soluble gel is subjected to a step wherein the sodium atoms of the sodium alginate molecules are substantially replaced by calcium atoms wherein the encapsulated bioactive agents precipitate to form solidified particles 50 (FIG. 11), and wherein the encapsulated bioactive agent aggregate 50 has the transmucosal delivery enhancing molecules (20) extending from the surface thereof.

Chemical analysis of this precipitated microencapsulated bioactive agent (50 in FIG. 11) has revealed a portion of the conjugated "spike" molecule 20 (e.g., the isoprenoid) is actually internalized bestowing resistance to intestinal disintegration. In fact, in its transmucosal specific configuration, whether in the soluble gel (sodium) alginate form or the precipitated (calcium) alginate form, the bioactive transport vehicle is even insoluble in the harshest of organic solvents and must be enzymatically digested with serum lipases for HPLC analysis of bioactive concentrations. In essence this comprises a delivery vehicle which is resistant to both gastric and intestinal disintegration and capable of delivering virtually 100% of the bioactive agent directly into the blood serum of the intestinal wall. Upon entering the blood serum, by route of the natural lipid uptake mechanism of the intestine, the serum-specific microencapsulate generally disintegrates within 15 minutes. In addition to therapeutic desposition within the blood serum, the soluble gel transport vehicle, (FIG. 10) or the solid vehicle (FIG. 11), also delivers a dose of a therapeutically or nutriceutically important molecule, such as the isoprenoid. For example, when lycopene is the transmucosal delivery enhancing molecule, lycopene is released in its biologically active form upon lipase digestion of the vehicle within the serum.

Figure 13:
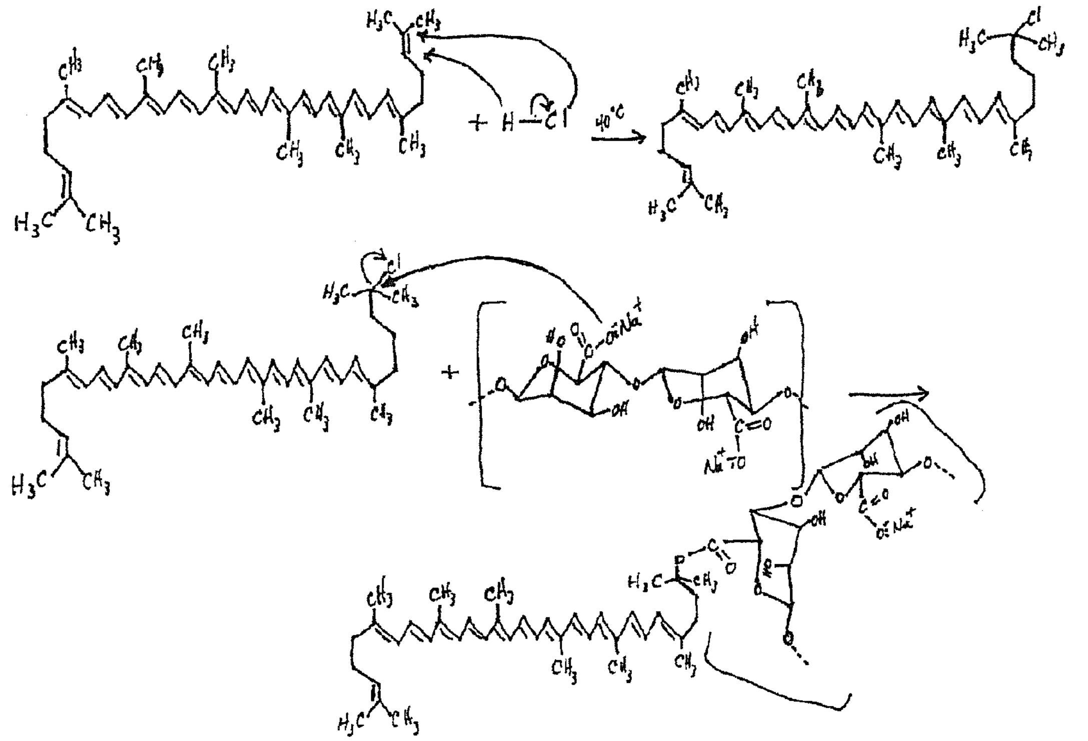
FIG. 13 is a diagram showing how lycopene (an isoprenoid) is covalently linked via a carboxyl group to the alginate backbone of the delivery vehicle.
Figure 14A:
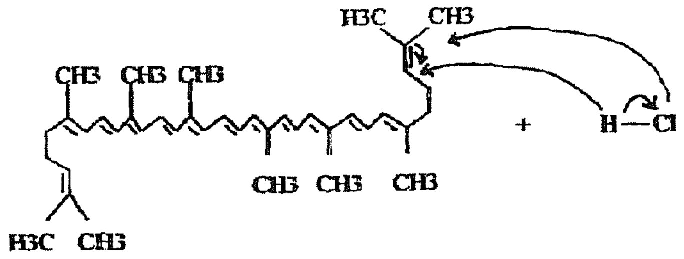
FIG. 14A is a diagram showing one embodiment of the chlorination of a lycopene molecule by HCl.
Figure 14B:
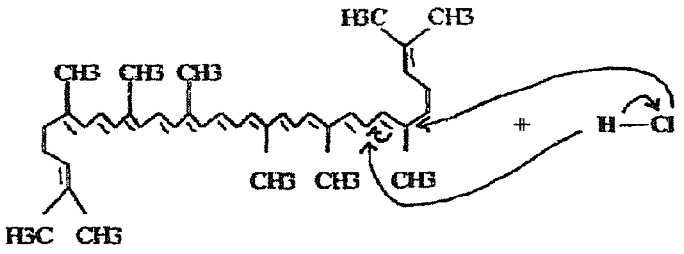
FIG. 14B is a diagram showing an alternative embodiment of the chlorination of a lycopene molecule by HCl.
Figure 14C:
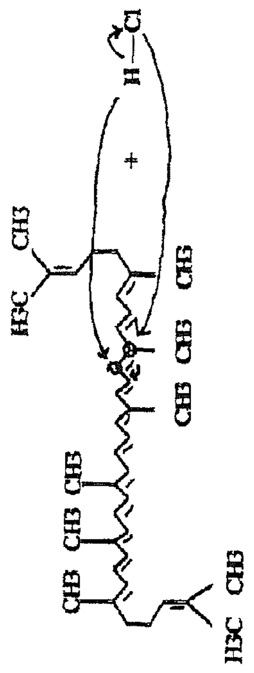
FIG. 14C is a diagram showing an alternative embodiment of the chlorination of a lycopene molecule by HCl.
Figure 14D:
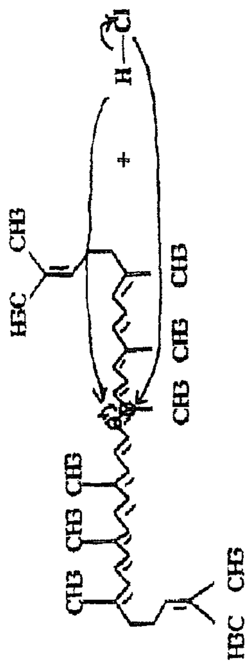
FIG. 14D is a diagram showing an alternative embodiment of the chlorination of a lycopene molecule by HCl.
Figure 14E:
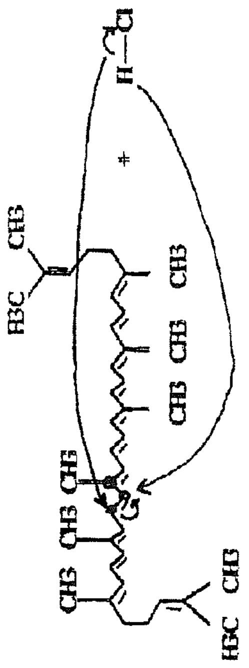
FIG. 14E is a diagram showing an alternative embodiment of the chlorination of a lycopene molecule by HCl.
Figure 14F:
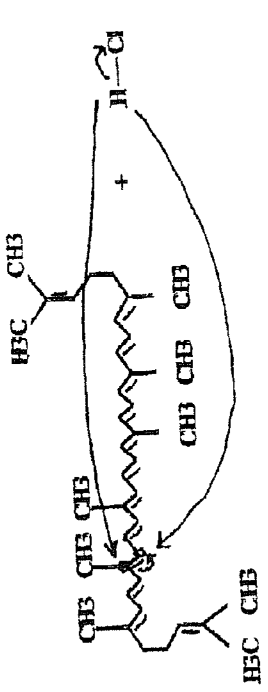
FIG. 14F is a diagram showing an alternative embodiment of the chlorination of a lycopene molecule by HCl.
Figure 14G:
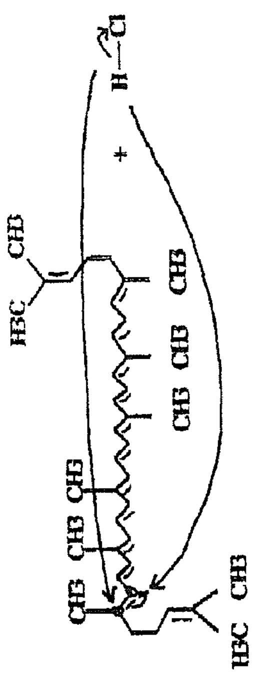
FIG. 14G is a diagram showing an alternative embodiment of the chlorination of a lycopene molecule by HCl.
Figure 14H:
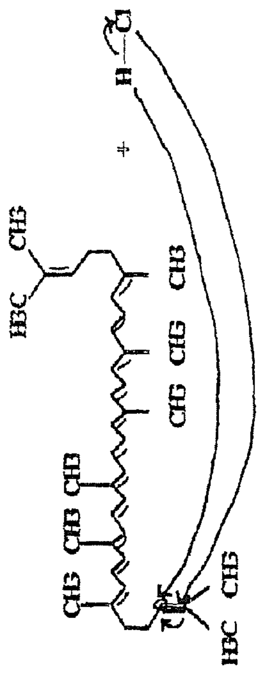
FIG. 14H is a diagram showing an alternative embodiment of the chlorination of a lycopene molecule by HCl.

An isoprenoid is easily conjugated to the alginate backbone of the transport vehicle by first converting it to its alkylhalide derivative. In one method of the presently claimed and disclosed inventive concept(s), the isoprenoid is prepared for conjugation so the alginate molecule by converting it to an alkylhalide derivative, such as by addition of hydrogen chloride to one of the unsaturated portions of the isoprenoid molecule (as shown in FIGS. 14A-14H, for example). However, the conversion is not limited to a chloride derivative and any halide (e.g., chloride, bromide, iodine) can be used. The reaction takes place rapidly at room temperature and addition follows Markovnikov rule, the hydrogen of the acid attaches to the carbon bearing the greatest number of hydrogens. The halide derivative can then be covalently conjugated to the alginate molecule, for example by the reaction mechanism shown in a non-limiting embodiment in FIG. 13.

Once the halide derivative of the isoprenoid is generated it is reacted with sodium alginate at a suitable temperature, such as 40° C. (or from 30° C. to 50° C.), for example, for a suitable period such as 20 minutes. The isoprenoid-alginate conjugate gel, as represented in FIG. 9, is then used as encapsulation polymer in the manufacture of a serum-specific therapeutic transport vehicle 40 as shown in FIG. 10, and then as discussed elsewhere herein may be further treated with calcium chloride to form a solid precipitate 50 (FIG. 11).

Alternatively, after formation of the encapsulated bioactive agent, and before treatment with calcium chloride solution, the isoprenoid-alginate can be mixed with, for example, carrageenan, xanthan gum, and/or agar-agar, and water and any other component useful as a thickener or cross-linking agent in the encapsulation of a particular bioactive agent and homogenized into a gel. Alternatively, the addition of the carrageenan, xanthan gum, or other component or agar agar may occur before the bioactive agent is added and the mixture is again homogenized to a homogeneous gel state. The bioactive agent may then be encapsulated by the combined polymer mixture. The gel may then be used in this form, in a dosage form or may be then loaded in an atomizer and spray atomized into a pool of aqueous calcium chloride solution (or other solution which may serve a similar purpose) at an appropriate temperature, for example at or below room temperature.

Immediately upon contact with the aqueous calcium chloride solution, the sodium (or potassium) of the alginate polymer is replaced by calcium and an instantaneous solidified microencapsulated sphere or particle 50 results (FIG. 11). The microencapsulated sphere or particle thus produced precipitates to the surface of the aqueous collectant and is then filtered off and dried, preferably to a moisture content of <1.0%, for example, or to an anhydrous state as explained in further detail below. The microencapsulated composition thus formed may then be incorporated into a capsule, tablet, or powder or other form for oral dosage or into the matrix of a functional food or beverage, to list but a few possibilities.

The presently claimed and disclosed inventive concept(s) is directed in particular to an oral polymeric delivery vehicle for transmucosal delivery of a bioactive agent in a mammalian subject which comprises a bioactive agent which is encapsulated by a polymeric coating, wherein the polymeric coating comprises molecules of an alginate and transmucosal delivery enhancing molecules, wherein the transmucosal delivery enhancing molecules are covalently conjugated to the alginate molecules, wherein the polymeric delivery vehicle is resistant to degradation within the stomach and within the lumen of the small intestine, and wherein the polymeric delivery vehicle is capable of transmucosal passage across the intestinal mucosa into the intestinal bloodstream wherein the polymeric delivery vehicle comprising the alginate molecules and transmucosal delivery enhancing molecules covalently conjugated thereto is degraded to release substantially all of the bioactive agent into the intestinal bloodstream.

The alginate may comprise sodium alginate, potassium alginate, and/or calcium alginate. The alginate molecules may be cross-linked. The transmucosal delivery enhancing molecules may comprise at least one of an isoprenoid compound, a vitamin, a signal peptide, or a fatty acid having 6-28 carbon atoms. The transmucosal delivery enhancing molecules may comprise at least one of lycopene, limonene, gamma-tocotrienol, geraniol, carvone, farnesol, geranylgeraniol, squalene or other linear terpenoids, a carotenoid, taxol, vitamin E, vitamin A, beta-carotene, Coenzyme $Q_{10}$ (ubiquinone), astaxanthin, zeaxanthin, lutein, citranxanthin, beta-choro-carotene, and canthroaxanthan. The polymeric delivery vehicle may further compriseat least one of a gum, a gum resin, a resin, glycerin, high fructose corn syrup, and a fruit or vegetable juice. The polymeric delivery vehicle may compriseat least one of the group comprising cellulose gums, pectins, pectin resins, locust bean gums, locust bean resins, xanthan gums, xanthan gum resins, carrageenans, sodium salts of carrageenans, gellan gums, gellan gum resins, whey protein gums, whey protein resins, agar agar, propylene glycol, Arabic gums, Arabic gum resins, guar gum, guar gum resins, gum tragacanth, and gum ghatti. The aqueous base may comprise water, and at least one of glycerin, a surfactant, or propylene glycol. The oil base may comprise at least one of soybean oil, peanut oil, sesame oil, safflower oil, canola oil, cotton seed oil, olive oil, corn oil, and/or vegetable oil. The absorbent factor may comprise at least one of glycyrrhizinate, glycrrhetinic acid, sucrose fatty acid ester, glycerin, glycerol fatty acid ester, adipic acid, polyethylene glycol, sodium dodecyl sulfate, sodium caprate, and sodium deoxycholate, sodium chloride, potassium chloride, calcium chloride or any combination thereof. The bioactive agent may comprise at least one of an antibiotic, an antiviral agent, a protease inhibitor, a polypeptide, a chemotherapeutic agent, an anti-tumor agent, an anti-sense drug, insulin, an RNA, a DNA, an immunosuppressant, a vaccine, a protein, a microorganism, a peptidomimetic, or nutriceutical. The aqueous or oil base may comprise <1% to 80% of the composition by weight. The transmucosal delivery enhancing molecules may comprise <0.5% to 30% of the vehicle by weight. The pH modulator and/or protease inhibitor may comprise <0.5% to 10% of the vehicle by weight. The polymeric coating may range in the size of 1 nm to 10 μm in diameter. The polymeric delivery vehicle may have a gel consistency or a solid consistency.

In another embodiment the presently claimed and disclosed inventive concept(s) is directed to a method of forming an oral polymeric delivery vehicle for transmucosal delivery of a bioactive agent, comprising providing an aqueous alginate gel comprising alginate molecules; providing transmucosal delivery enhancing molecules comprising isoprenoid molecules or medium or long chain fatty acid molecules; combining and mixing the aqueous alginate gel with the transmucosal delivery enhancing molecules under temperature conditions such that the transmucosal delivery enhancing molecules become covalently conjugated to the alginate molecules to form a polymeric coating mixture; and combining and mixing the polymeric coating mixture with a bioactive agent wherein the bioactive agent becomes encapsulated by the polymeric coating to form the polymeric delivery vehicle containing the bioactive agent, and wherein the polymeric delivery vehicle is substantially resistant to degradation within the stomach and intestinal lumen and is able to be passed into the intestinal mucosa before degradation of the polymeric coating and release of the bioactive agent into the intestinal mucosal bloodstream.

In the method, the transmucosal delivery enhancing molecules may comprise at least one of lycopene, limonene, gamma-tocotrienol, geraniol, carvone, farnesol, geranylgeraniol, squalene and other linear terpenoids, carotenoids, taxol, vitamin E, vitamin A, beta-carotene, citranxanthin, beta-choro-carotene, and canthraxanthan. The method may comprise mixing the polymeric coating mixture or the encapsulated delivery vehicle with at least one of carrageenan, xanthan gum or agar agar. The method may further comprise combining the polymeric delivery vehicle with a cross-linking agent to form a solid polymeric delivery vehicle. The cross-linking agent may be calcium chloride, calcium acetate, or aluminum sulfate.

The presently claimed and disclosed inventive concept(s) is described herein in connection with certain preferred embodiments among the following description and description elsewhere herein and by examples so that aspects thereof may be more fully understood and appreciated, however it is not intended to limit the presently claimed and disclosed inventive concept(s) to these particular examples or embodiments. On the contrary, it is intended to cover all alternatives, modifications and equivalents as may be included within the scope of the presently claimed and disclosed inventive concept(s) as defined by the claims herein. Thus, the following examples will serve to illustrate the practice of this presently claimed and disclosed inventive concept(s), it being understood that the particulars shown are by way of example and for purposes of illustrative discussion of preferred embodiments of the presently claimed and disclosed inventive concept(s) only and are presented in the cause of providing what is believed to be the most useful and readily understood description of formulation procedures as well as of the principles and conceptual aspects of the presently claimed and disclosed inventive concept(s).

EXAMPLES

Example 1

Conversion of Lycopene into a Lycopene Halide, and Encapsulation of $CoQ_{10}$ Using lycopene crystals obtained from Sigma-Aldrich, 1 mol of lycopene is reacted with one mol of HCl, thus adding one hydrogen atom and one chlorine atom to a terminal end unsaturation of the lycopene molecule. There are a number of halide by products possible here. However, the positioning of the halide conversion, at least initially will not be of great concern.

$$C_{40}H_{56}+HCl=C_{40}H_{57}Cl \quad (1)$$

As indicated in the above empirical equation, 1 mol of lycopene is required to react with 1 mol of HCl. Furthermore, to generate the hydrogen chloride from a reaction between sodium chloride and sulfuric acid one reacts 1 mol of sulfuric acid with 1 mol of NaCl to get 1 mol of HCl.

As can be seen from its molecular structure in FIG. 6, lycopene may be classified chemically as a conjugated diene. However, without wishing to be bound by theory, we may still expect it to react according to those mechanisms which apply to alkenes. Thus, with the addition of hydrogen halide we expect a regioselective, following the Markovnikov rule, mechanism in which the hydrogen of the acid will attach itself to the carbon that already holds the greater number of hydrogen. In the case of the addition of hydrogen halide to lycopene we find that this rule will apply and therefore we can accurately predict the principle products of this reaction. Without wishing to be bound by theory, we will explore this more closely by taking a look at the reaction mechanism. To gain a better understanding of the reaction, it can be observed that the lycopene molecule is highly unsaturated, comprising 13 carbon-carbon double bonds. The molecule is classified as a hydrocarbon with the carbon-carbon double bonds comprising its centers of reactivity.

Next to gain a fundamental understanding of the reaction mechanism we must then ask what types of reactions can we expect out of the carbon-carbon double bond? The double bond consists of a strong bond and a weak bond. We may therefore expect a reaction to involve a breaking of this weaker bond of the double bond. The double bond is broken and two strong single bonds are formed in its place. Therefore we know the type of reaction the double bond undergoes is an addition reaction. In an addition reaction, reagent is simply added to substrate.

The mechanism for the regioselective addition of hydrogen halide to the lycopene molecule indicates an end result of several different addition configurations (FIG. 14A-14H). Equal proportions of the different addition products are not likely, furthermore, it is difficult at best not only to predict which products will predominate but to isolate any one of the products in highly pure form. However, for the purposes of the presently claimed and disclosed inventive concept(s), one addition product is just as functional as another and the primary goal is to covalently link the lycopene isoprenoid unit (or other isoprenoid molecule) to a mole of alginate polymer.

Figure 12:
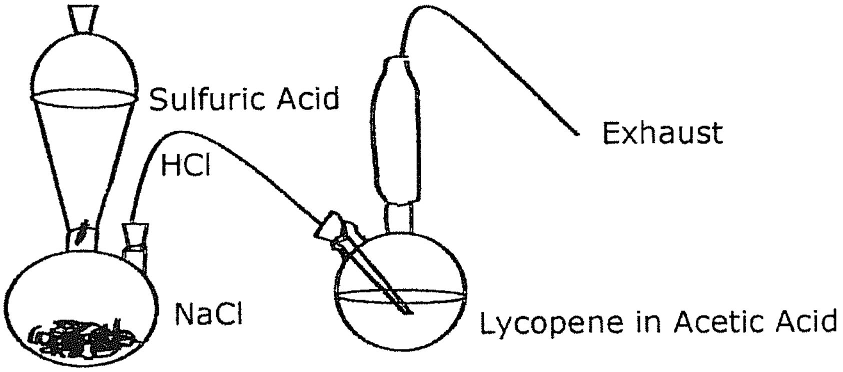
FIG. 12 is a diagram of an apparatus for the conversion of an isoprenoid to its derivative hydrogen halide by exposure to gaseous HCl produced from a reaction of sulfuric acid with sodium chloride.

In the addition of hydrogen halide (e.g., hydrogen chloride, hydrogen bromide, or hydrogen iodide) to an isoprenoid unit, the reaction is frequently carried out by passing the dry gaseous hydrogen halide directly into a solution of the isoprenoid. The moderately polar solvent, acetic acid, which will dissolve both the polar hydrogen halide and the non-polar isoprenoid molecule, is sometimes used to bring both molecules into the reaction phase. The familiar aqueous solutions of hydrogen halides are not generally used, in part, this is to avoid the addition of $H_2O$ to the isoprenoid unit. In the present reaction, in a preferred embodiment, >98% of lycopene crystals are dissolved in a minimum amount of hexane/methanol solvent and pass dry gaseous hydrogen chloride directly into this solution. It is understood that there are more efficient and safer ways of adding HCl to an isoprenoid, one skilled in the art will recognize this. We simply use this reaction as an "old-school" preference. We can generate hydrogen chloride, in one embodiment, by allowing concentrated sulfuric acid to react with sodium chloride for example by using an apparatus as shown in FIG. 12.

Procedure: Microencapsulation of $CoQ_{10}$

In a 250 ml reaction vessel dissolve 1.0 g of lycopene in 100 ml of hexane and add 25 ml of methanol. Stir the mixture mildly until all the lycopene is dissolved. Next, using the HCl generator, add 20.0 g of NaCl to the generator and 10 ml of concentrated sulfuric acid to the separatory funnel of the generator. Run the bubbler into the reaction vessel and begin releasing eh $H_2SO_4$ dropwise into the NaCl. Allow the reaction to run to completion with periodic swirling of the reaction vessel. Upon completion of the reaction collect the precipitated lycopene chloride by vacuum filtration and wash the solid 3 times with distilled water.

Next in a 1000 ml beaker add 40.62 g of sodium alginate to 4700 ml of cold distilled water and homogenize until a gel is formed. Then add 0.76 g of lycopene chloride and agitate at 40-50° C. for a period of 20 minutes. Allow the solution to cool to room temperature. Dissolve 2.5 g of 99.99% $CoQ_{10}$ in 3 ml of Tween 20® and add it to the gel solution. Homogenize as to mix completely. Atomize the encapsulate gel to a fine powder, collect by filtration on a 200 mesh stainless screen and dry to an anhydrous state in a vacuum drier.

Example 2

Oral Formulation of Humulin R Insulin

Reagents

| | |
|---|---|
| 1. Lycopene-Alginate | 97.4 (for example, as prepared in Example 1) |
| 2. Xanthan Gum | 1.0 g |
| 3. Calcium Chloride | 23.0 g |
| 4. Distilled water | 100.0 ml |

In a 5 gallon container add 1.5 gallons of distilled water, 97.4 g of lycopene alginate and 1.0 g of xanthan gum. Homogenize this mixture to a complete gel. Next weigh 23.0 g of calcium chloride into a 250 ml beaker and to this add 100 ml of distilled water. Allow the calcium salt to dissolve completely before proceeding.

Next, add 0.5 ml of insulin water (1 unit/0.5 ml) into a 2 ml sterile centrifuge tube. Add 1.5 ml of encapsulation gel as prepared above and homogenize completely for a period of 10 minutes. Next, using a sterile 3 ml syringe equipped with a 2 inch 14 gage needle, draw the Insulin gel encapsulate into the syringe and slowly decant it drop-wise into the 100 ml of calcium chloride water. Allow the encapsulate spheres to cure in the water for a period of 30 minutes. Collect the spheres by vacuum filtration and wash them 3 times with a 50 ml portion of sterile water. Dry the beads to an anhydrous state by vacuum drying. This represents a single dose delivering 1 unit of insulin.

Three doses of insulin in water were encapsulated for rat dosing. Free insulin was used as control. Rats were used for in vivo dosing. The rats were clearly diabetic upon dosing having glucose concentrations of >350.20. Minutes after dosing with the serum-specific microencapsulate insulin beads, a 100 point decrease in glucose concentration was detected and maintained through the final blood draw which was conducted four hours after dosing.

Example 3

Encapsulation of Probiotic Bacteria 250 ml 1% alginate solution prepared with 2 g dextrose to 0.5 g yeast extract per 100 ml. The solution was split into 125 ml beakers. Beaker A was mixed with 20 g *Lactobacillus acidophilus*. The solution was sprayed with atomizer gun into 750 ml $CaCl_2$ solution, the resulting liquid was forced through fine cotton cloth-solids collected in cloth. Cloth with solids was placed in a 1000 ml flask and put under vacuum for one hour. At 1 hour the cloth and solids were removed, solids appeared to be of anhydrous state, solids were collected giving 11.13 g. Prepared as above, a *Bifidiobacterium* 125 ml solution was sprayed into a 600 ml $CaCl_2$ solution 625 ml of liquid was collected after solids were strained through cotton cloth. The wet weight of cloth and solids was 38.756 g. The cloth and solids were placed in a flask and under vacuum. After one hour the sample was removed. Solids were scraped from the cloth and weighed giving a sample weight of 16.947 g; this was dried to anhydrous.

Example 4

Preparation of a Purified Beta-Chloro-Carotene (BCC)

In a 1000 mL one-neck round bottom flask, add 416 g of 30% beta-carotene oil. Add 75 g of sodium chloride to the round bottom flask of HCL generator and 75 ml of concentrated sulfuric acid to the separatory funnel portion of the generator. Attach the outlet line to the reaction vessel and connect the exhaust outlet from the reaction to an exhaust line. Open the separatory valve until a rate of 10-20 drops/second of sulfuric acid is established. If the reaction gets too violent, close the valve till it settles. Allow the reaction to continue until all of the acid is run-off into the sodium chloride and until the reaction within the sodium chloride has slowed to 5-8 bubbles/second. Carefully remove the HCL generator and cautiously rinse both the separatory and sodium chloride reservoirs using acceptable chemical waste protocols. Collect the red BCC oil in a large amber bottle, use a funnel to fill the bottle, cap and store at 4-8° C. until use. Yield 438.0 g, concentration=0.30 g Pure BCC/g of oil.

Example 5

Alternate Preparation of Beta-Chloro-Carotene

Same as in Example 4 above however, in this example 125 g of 99.98% beta-carotene was used. Yield 147.0 g, concentration=99.0% BCC.

Example 6

Preparation of Beta-Chloro-Carotene-Sodium Alginate Conjugate

In a 55 gallon stainless steel circulator mixer add 28 gallons of distilled water. Turn on the high shear pump and slowly begin adding a total of 4.87 kg of sodium alginate. Homogenize to a complete gel (gelation is complete when there is an absence of clumps or particulates and a clearing of the mixture). Once gelation is complete add 126.7 g of BCC, 30% oil and using a 55 gallon submersible heating element, heat the polymer, under homogenation, at 40-50° C. for a period of 20 minutes. Allow the solution to cool to room temperature to form a covalently conjugated BCC-sodium alginate polymer. Next, using the homogenizer as a transfer pump, transfer the BCC-alginate polymer into 5-gallon atomizer pails, 4.5 gallons/pail and load one 5-gallon pail at a time onto the atomization unit. Next prepare 20 gallons of aqueous collectant by dissolving 16.63 kg of calcium chloride into 20 gallons of distilled water in a 110 gallon atomization tank. Agitate until all the solids have dissolved and allow the calcium chloride solution to cool to 40° C. Next, working with one 5-gallon pail of BCC-alginate polymer gel at a time, atomize the entire lot of BCC-sodium alginate polymer gel directly into the aqueous calcium chloride solution. This causes precipitation of the BCC-alginate polymer. Upon completion of the atomization process immediately collect the wet precipitated BCC-calcium alginate polymer by gravity filtration on a 100 mesh stainless steel screen atop the 100 gallon collection vessel. Next transfer the wet precipitated solids into 40 gallons of distilled water within the 100 gallon wash tank. Agitate the solids washing them for a period of 10 minutes and then re-collect them by gravity filtration on top the 100 mesh stainless screen of the 100 gallon filtration vessel. Transfers between the atomization tank, filtration and wash tanks should be conducted with the aid of a sanitary transfer pump. A yield of 39.2 kg of 0.76 g/100 g of the BCC conjugated calcium alginate was obtained from this process.

Example 7

Production of Microencapsulated $CoQ_{10}$ (Coenzyme $Q_{10}$)

In a 55 gallon stainless steel circulator mixer add 12.3 gallons of distilled water. Turn on the high shear pump and slowly begin adding a total of 2.05 kg of sodium alginate. Homogenize to a complete gel (gelation is complete when there is an absence of clumps and particulates and a clearing of the mixture). Once gelation is complete add 50.7 g of 30% beta-chloro-carotene oil, and using a 55 gallon submersible heating element, heat the polymer, under homogenation, at 40-50° C. for a period of 30 minutes to form a BCC-alginate polymer. Alternatively, another isoprenoid or fatty acid compound can be use for conjugation to the alginate, as contemplated and described elsewhere herein. Allow the solution to cool to room temperature. Once cooled to room temperature, add 3 kg of 99% $CoQ_{10}$ and again using the high shear pump blend the product to a homogenous gel comprising $CoQ_{10}$ encapsulated by the BCC-alginate polymer (gelation is complete when there is an absence of clumps or particulates). Next, using the homogenizer as a transfer pump, transfer the encapsulated $CoQ_{10}$ to 5-gallon atomizer pails and load one 5-gallon pail at a time onto the atomization unit. Next prepare 20 gallons of aqueous collectant by dissolving 16.63 kg of calcium chloride into 20 gallons of distilled water in a 110 gallon atomization tank. Agitate until all the solids have dissolved and allow the calcium chloride solution to cool to 40° C. Next, working with one 5-gallon pail of $CoQ_{10}$ encapsulated gel at a time, atomize the entire lot of encapsulated directly into the aqueous calcium chloride collectant. This causes precipitation of the encapsulated $CoQ_{10}$. Upon completion of the atomization process immediately collect the wet precipitated encapsulated $CoQ_{10}$ by gravity filtration on a 80 mesh stainless steel screen atop the 100 gallon collection vessel. Next transfer the wet precipitated encapsulated $CoQ_{10}$ solids into 20 gallons of distilled water within the 100 gallon wash tank. Agitate the solids washing them for a period of 10 minutes and then re-collect them by gravity filtration on top the 80 mesh stainless screen of the 100 gallon filtration vessel. Transfers between the atomization tank, filtration and wash tanks should be conducted with the aid of a sanitary transfer pump. A yield of 4.72 kg of BCC-alginate microencapsulated $CoQ_{10}$ (60% $CoQ_{10}$) was obtained.

Example 8

Production of Microencapsulated Vitamin C

In a 55 gallon stainless steel circulator mixer add 28 gallons of distilled water. Turn on the high shear pump and slowly begin adding a total of 4.33 kg of sodium alginate. Homogenize to a complete gel (gelation is complete when there is an absence of clumps or particulates and a clearing of the mixture). Once gelation is complete add 112.83 g of beta-chloro-carotene 30% oil and using a 55 gallon submersible heating element, heat the polymer, under homogenation, at 40°-50° C. for a period of 30 minutes thereby forming a BCC-alginate polymer. Alternatively, another isoprenoid or fatty acid compound can be use for conjugation to the alginate, as contemplated and described elsewhere herein. Allow the solution to cool to room temperature. Once cooled to room temperature, add 6.68 kg of ascorbic acid (vitamin C) and again using the high shear pump blend the product to a homogeneous gel comprising the ascorbic acid encapsulated by the BCC-alginate polymer (gelation is complete when there is an absence of clumps or particulates). Next, using the homogenizer as a transfer pump, transfer the encapsulated vitamin C into 5-gallon atomizer pails, and load one 5-gallon pail at a time onto the atomization unit. Next prepare 20 gallons of aqueous collectant by dissolving 16.63 kg of calcium chloride into 20 gallons of distilled water in a 110 gallon atomization tank. Agitate until all the solids have dissolved and allow the calcium chloride solution to cool to 40° C. Next, working with one 5-gallon pail of the resulting gel at a time, atomize the entire lot of encapsulated vitamin C directly into the aqueous calcium chloride collectant. This causes precipitation of the encapsulated Vitamin C. Upon completion of the atomization process immediately collect the wet precipitated encapsulated vitamin C by gravity filtration on a 100 mesh stainless steel screen atop the 100 gallon collection vessel. Next transfer the wet precipitated encapsulated vitamin C solids into 40 gallons of distilled water within the 100 gallon wash tank. Agitate the solids washing them for a period of 10 minutes and then re-collect them by gravity filtration on top the 80 mesh stainless screen of the 100 gallon filtration vessel. Transfers between the atomization tank, filtration and wash tanks should be conducted with the aid of a sanitary transfer pump. A 10.52 kg yield of BCC-alginate microencapsulated vitamin C (60% vitamin C) was obtained.

Example 9

Production of Microencapsulated Resveratrol

In a 55 gallon stainless steel circulator mixer add 30 gallons of distilled water. Turn on the high shear pump and slowly begin adding a total of 2.17 kg of sodium alginate. Homogenize to a complete gel (gelation is complete when there is an absence of clumps and particulates and a clearing of the mixture). Once gelation is complete add 56.5 g of beta-chloro-carotene and using a 55 gallon submersible heating element, heat the polymer, under homogenation, at 40°-50° C. for a period of 30 minutes thereby forming the BCC-alginate polymer. Alternatively, another isoprenoid or fatty acid compound can be use for conjugation to the alginate, as contemplated and described elsewhere herein. Allow the solution to cool to room temperature. Once cooled to room temperature, add 3.34 kg of resveratrol and again using the high shear pump blend the product to a homogeneous gel forming the resveratrol encapsulated by the BCC-alginate polymer (gelation is complete when there is an absence of clumps or particulates). Next, using the homogenizer as a transfer pump, transfer the encapsulated resveratrol to 5-gallon atomizer pails, and load one 5-gallon pail at a time onto the atomization unit. Next prepare 20 gallons of aqueous collectant by dissolving 16.63 kg of calcium chloride into 20 gallons of distilled water in a 110 gallon atomization tank. Agitate until all the solids have dissolved and allow the calcium chloride solution to cool to 40° C. Next, working with one 5-gallon pail of encapsulated gel at a time, atomize the entire lot of encapsulated resveratrol directly onto the aqueous calcium chloride collectant. This causes precipitation of the encapsulated resveratrol. Upon completion of the atomization process immediately collect the wet precipitated encapsulated resveratrol solids by gravity filtration on an 80 mesh stainless steel screen atop the 100 gallon collection vessel. Next transfer the wet precipitated encapsulated resveratrol solids into 40 gallons of distilled water within the 100 gallon wash tank. Agitate the solids washing them for a period of 10 minutes and then re-collect them by gravity filtration on top the 80 mesh stainless screen of the 100 gallon filtration vessel. Press the solids dry. Transfers between the atomization tank, filtration and wash tanks should be conducted with the aid of a sanitary transfer pump. A yield of 5.7 kg of BCC-alginate microencapsulated resveratrol (60% resveratrol) was obtained from this process.

Example 10

Production of Microencapsulated Pregnenolone Formulation

In a 55 gallon stainless steel circulator mixer add 12.3 gallons of distilled water. Turn on the high shear pump and slowly begin adding a total of 1.48 kg of sodium alginate. Homogenize to a complete gel (gelation is complete when there is an absence of clumps and particulates and a clearing of the mixture). Once gelation is complete add 11.4 g of 99% beta-chloro-carotene powder and using a 55 gallon submersible heating element, heat the polymer, under homogenation, at 40°-50° C. for a period of 30 minutes thereby forming the BCC-alginate polymer. Alternatively, another isoprenoid or fatty acid compound can be use for conjugation to the alginate, as contemplated and described elsewhere herein. Allow the solution to cool to room temperature. Once cooled to room temperature, add 2.25 kg of pregnenolone and again using the high shear pump blend the product to a homogeneous gel comprising the pregnenolone encapsulated by the BCC-alginate polymer (gelation is complete when there is an absence of clumps or particulates). Next, using the homogenizer as a transfer pump, transfer the encapsulated pregnenolone to three 5-gallon atomizer pails, (4.2 gallons/pail) and load one 5-gallon pail at a time onto the atomization unit. Next prepare 20 gallons of aqueous collectant by dissolving 16.63 kg of calcium chloride into 20 gallons of distilled water in a 110 gallon atomization tank. Agitate until all the solids have dissolved and allow the calcium chloride solution to cool to 40° C. Next, working with one 5-gallon pail of the resulting gel at a time, atomize the entire lot of encapsulated pregnenolone directly into the aqueous calcium chloride collectant. This causes precipitation of the encapsulated pregnenolone. Upon completion of the atomization process immediately collect the wet precipitated encapsulated pregnenolone by gravity filtration on an 80 mesh stainless steel screen atop the 100 gallon collection vessel. Next transfer the wet precipitated encapsulated pregnenolone encapsulated solids into 20 gallons of distilled water within the 100 gallon wash tank. Agitate the solids washing them for a period of 10 minutes and then re-collect them by gravity filtration on top the 80 mesh stainless screen of the 100 gallon filtration vessel. Transfers between the atomization tank, filtration and wash tanks should be conducted with the aid of a sanitary transfer pump. A 3.2 kg yield of BCC-alginate microencapsulated pregnenolone (60% pregnenolone) was obtained from this process.

Example 11

Production of Microencapsulated Mixed Antioxidant Formulation

In a 55 gallon stainless steel circulator mixer add 40 gallons of distilled water. Turn on the high shear pump and slowly begin adding a total of 13.67 kg of sodium alginate. Homogenize to a complete gel (gelation is complete when there is an absence of clumps or particulates and a clearing of the mixture). Once gelation is complete add 103.89 g of 99% BCC powder and using a 55 gallon submersible heating element, heat the polymer, under homogenation, at 40°-50° C. for a period of 30 minutes thereby forming a BCC-alginate polymer. Alternatively, another isoprenoid or fatty acid compound can be use for conjugation to the alginate, as contemplated and described elsewhere herein. Allow the solution to cool to room temperature. Once cooled to room temperature, add 5 kg of lycopene, 5 k of lutein, 10 kg astaxanthin and 500 g of beta-carotene, 3 kg of cranberry extract, and 3 kg of bilberry extract (or any other combination of antioxidants) and again using the high shear pump blend the product to a homogeneous gel comprising the mixed antioxidants encapsulated by the BCC-alginate polymer (gelation is complete when there is an absence of clumps or particulates). Next, using the homogenizer as a transfer pump, transfer the encapsulated antioxidants to 5-gallon atomizer pails, and load one 5-gallon pail at a time onto the atomization unit. Next prepare 20 gallons of aqueous collectant by dissolving 16.63 kg of calcium chloride into 20 gallons of distilled water in a 110 gallon atomization tank. Agitate until all the solids have dissolved and allow the solution calcium chloride to cool to 40° C. Next, working with one 5-gallon pail of encapsulated gel at a time, atomize the entire lot of encapsulated antioxidant mixture directly into the aqueous calcium chloride collectant. This causes precipitation of the encapsulated antioxidants. Upon completion of the atomization process immediately collect the wet precipitated encapsulated antioxidants by gravity filtration on a 150 mesh stainless steel screen atop the 100 gallon collection vessel. Next transfer the wet precipitated encapsulated antioxidant solids into 40 gallons of distilled water within the 100 gallon wash tank. Agitate the solids washing them for a period of 10 minutes and then re-collect them by gravity filtration on top the 150 mesh stainless screen of the 100 gallon filtration vessel. Press the solids dry. Transfers between the atomization tank, filtration and wash tanks should be conducted with the aid of a sanitary transfer pump. A yield of 39.8 kg of BCC-alginate microencapsulated mixed-antioxidant formulation (60% antioxidants) was obtained from this process.

Although the presently claimed and disclosed inventive concept(s) and its advantages have been described in detail, it should be understood that various changes, substitutions and alterations can be made herein without departing from the spirit and scope of the presently claimed and disclosed inventive concept(s) as defined by the appended claims. Moreover, the scope of the present application is not intended to be limited to the particular embodiments of the process, formulas, compounds, compositions of matter, means, methods, mechanisms and steps described in the specification. As one of ordinary skill in the art will readily appreciate from the disclosure of the presently claimed and disclosed inventive concept(s), processes, formulas, compounds, compositions of matter, means, mechanisms, methods, or steps, presently existing or later to be developed that perform substantially the same function or achieve substantially the same result as the corresponding embodiments described herein may be utilized according to the present invention. Accordingly, the appended claims are intended to include within their scope such processes, formulas, compounds, compositions of matter, means, mechanisms, methods, or steps.

Each of the references, patents or publications cited herein is expressly incorporated herein by reference in its entirety. Also incorporated herein by reference in their entireties are U.S. Provisional Application Ser. Nos. 60/582,632 and 60/582,633 and U.S. patent application Ser. Nos. 11/166,385 and 12/648,901.

The invention claimed is:

1. An oral polymeric delivery vehicle for transmucosal delivery of a bioactive agent in a mammalian subject, comprising:

a bioactive agent which is encapsulated by a polymeric coating, wherein the polymeric coating comprises molecules of alginate and transmucosal delivery enhancing molecules, wherein the transmucosal delivery enhancing molecules are covalently conjugated to the alginate molecules and extend from the surface of the polymeric coating, wherein the polymeric coating is resistant to degradation within the stomach and within the lumen of the small intestine, such that the polymeric delivery vehicle is capable of transmucosal passage across the intestinal mucosa into the intestinal bloodstream wherein the polymeric coating is degraded to release substantially all of the bioactive agent into the intestinal bloodstream; and wherein the transmucosal delivery enhancing molecules comprise at least one of an isoprenoid compound, a vitamin, or a fatty acid having 6-28 carbon atoms.

2. The polymeric delivery vehicle of claim 1, wherein the alginate molecules are cross-linked.

3. The polymeric delivery vehicle of claim 1, wherein said alginate is calcium alginate.

4. The polymeric delivery vehicle of claim 1, wherein the transmucosal delivery enhancing molecules comprise at least one of lycopene, limonene, gamma-tocotrienol, geraniol, carvone, farnesol, geranylgeraniol, squalene or other linear terpenoids, a carotenoid, taxol, vitamin E, vitamin A, beta-carotene, Coenzyme Q10 (ubiquinone), astaxanthin, zeaxanthin, lutein, citranxanthin, beta-choro-carotene, and canthroaxanthan.

5. The polymeric delivery vehicle of claim 1, further comprising at least one of a gum, a gum resin, a resin, glycerin, high fructose corn syrup, and a fruit or vegetable juice.

6. The polymeric delivery vehicle of claim 1, comprising at least one of the group comprising cellulose gums, pectins, pectin resins, locust bean gums, locust bean resins, xanthan gums, xanthan gum resins, carrageenans, sodium salts of carrageenans, gellan gums, gellan gum resins, whey protein gums, whey protein resins, agar agar, propylene glycol, Arabic gums, Arabic gum resins, guar gum, guar gum resins, gum tragacanth, and gum ghatti.

7. The polymeric delivery vehicle of claim 1, further comprising an aqueous base, wherein the aqueous base comprises water, and at least one of glycerin, a surfactant, or propylene glycol.

8. The polymeric delivery vehicle of claim 1, further comprising an oil base, wherein the oil base comprises at least one of soybean oil, peanut oil, sesame oil, safflower oil, canola oil, cotton seed oil, olive oil, corn oil, and/or vegetable oil.

9. The polymeric delivery vehicle of claim 1, further comprising an absorbent factor, wherein the absorbent factor comprises at least one of glycyrrhizinate, glycrrhetinic acid, sucrose fatty acid ester, glycerin, glycerol fatty acid ester, adipic acid, polyethylene glycol, sodium dodecyl sulfate, sodium caprate, and sodium deoxycholate, sodium chloride, potassium chloride, calcium chloride or any combination thereof.

10. The polymeric delivery vehicle of claim 1, wherein the bioactive agent comprises at least one of an antibiotic, an antiviral agent, a protease inhibitor, a polypeptide, a chemotherapeutic agent, an anti-tumor agent, an anti-sense drug, insulin, an RNA, a DNA, an immunosuppressant, a vaccine, a protein, a microorganism, a peptidomimetic, or nutriceutical.

11. The polymeric delivery vehicle of claim 1, wherein the transmucosal delivery enhancing molecules comprise <0.5% to 30% of the vehicle by weight.

12. The polymeric delivery vehicle according to claim 1, further comprising a pH modulator, protease inhibitor, or a combination thereof, wherein the pH modulator and/or protease inhibitor comprises <0.5% to 10% of the vehicle by weight.

13. The polymeric delivery vehicle of claim 1, wherein the polymeric delivery vehicle ranges in the size of 1 nm to 10 μm in diameter.

14. The polymeric delivery vehicle of claim 1, wherein the polymeric delivery vehicle has a gel consistency.

15. The polymeric delivery vehicle of claim 1, wherein the polymeric delivery vehicle has a solid consistency.

16. A method of forming an oral polymeric delivery vehicle for transmucosal delivery of a bioactive agent, comprising:

providing an aqueous alginate gel comprising alginate molecules;

providing transmucosal delivery enhancing molecules comprising isoprenoid molecules, vitamins, or medium or long chain fatty acid molecules;

combining and mixing the aqueous alginate gel with the transmucosal delivery enhancing molecules under temperature conditions such that the transmucosal delivery enhancing molecules become covalently conjugated to the alginate molecules to form a polymeric coating mixture;

combining and mixing the polymeric coating mixture with a bioactive agent wherein the bioactive agent becomes encapsulated by the polymeric coating to form the polymeric delivery vehicle containing the bioactive agent, and wherein the polymeric delivery vehicle is substantially resistant to degradation within the stomach and intestinal lumen and is able to be passed into the intestinal mucosa before degradation of the polymeric coating and release of the bioactive agent into the intestinal mucosal bloodstream.

17. The method of claim 16, wherein the transmucosal delivery enhancing molecules comprise at least one of lycopene, limonene, gamma-tocotrienol, geraniol, carvone, farnesol, geranylgeraniol, squalene and other linear terpenoids, carotenoids, taxol, vitamin E, vitamin A, beta-carotene, citranxanthin, beta-choro-carotene, and canthraxanthan.

18. The method of claim 16, comprising mixing the polymeric coating mixture or the encapsulated delivery vehicle with at least one of carrageenan, xanthan gum or agar agar.

19. The method of claim 16, further comprising combining the polymeric delivery vehicle with a cross-linking agent to form a solid polymeric delivery vehicle.

20. The method of claim 19, further comprising wherein the cross-linking agent is calcium chloride, calcium acetate, or aluminum sulfate.

* * * * *